US009315783B2

(12) United States Patent
Inouye et al.

(10) Patent No.: US 9,315,783 B2
(45) Date of Patent: Apr. 19, 2016

(54) CODON-OPTIMIZED GENE FOR MUTATED SHRIMP LUCIFERASE AND METHOD FOR USE THEREOF

(71) Applicant: JNC CORPORATION, Tokyo (JP)

(72) Inventors: Satoshi Inouye, Yokohama (JP); Junichi Sato, Yokohama (JP)

(73) Assignee: JNC CORPORATION, Tokyo (JP)

( * ) Notice: Subject to any disclaimer, the term of this patent is extended or adjusted under 35 U.S.C. 154(b) by 34 days.

(21) Appl. No.: 14/188,838

(22) Filed: Feb. 25, 2014

(65) Prior Publication Data

US 2014/0242574 A1 Aug. 28, 2014

(30) Foreign Application Priority Data

Feb. 28, 2013 (JP) ................. 2013-038350

(51) Int. Cl.
| | | |
|---|---|---|
| C12N 9/02 | (2006.01) |
| C12N 1/20 | (2006.01) |
| C12N 15/00 | (2006.01) |
| C07H 21/04 | (2006.01) |
| C12Q 1/66 | (2006.01) |

(52) U.S. Cl.
CPC ............... *C12N 9/0069* (2013.01); *C12Q 1/66* (2013.01); *C12Y 113/12013* (2013.01)

(58) Field of Classification Search
CPC ............ C12N 9/004; C12Q 1/66; C12Q 1/68; C12Y 113/12005
USPC .................... 435/189, 252.3, 320.1; 536/23.2
See application file for complete search history.

(56) References Cited

U.S. PATENT DOCUMENTS

| | | | |
|---|---|---|---|
| 7,723,502 B2 | 5/2010 | Coleman et al. |
| 8,557,970 B2 | 10/2013 | Encell et al. |
| 8,809,529 B2 * | 8/2014 | Klaubert | ............... C07D 487/04 544/350 |
| 2002/0102687 A1 | 8/2002 | Inouye |
| 2014/0223590 A1 | 8/2014 | Binkowski et al. |

FOREIGN PATENT DOCUMENTS

| | | |
|---|---|---|
| GB | 2425535 A | 11/2006 |
| GB | 2479847 A | 10/2011 |
| JP | 2002-320482 A | 11/2002 |
| JP | 4613441 B2 | 1/2011 |
| JP | 2012525819 A | 10/2012 |
| WO | WO-2004042010 A | 5/2004 |
| WO | WO-2010/127368 A1 | 11/2010 |
| WO | WO-2011007314 A1 | 1/2011 |
| WO | WO-2011025980 A1 | 3/2011 |
| WO | WO-2012061529 A1 | 5/2012 |
| WO | WO-2012061530 A2 | 5/2012 |
| WO | WO-2012061530 A3 | 9/2012 |
| WO | WO-2012061530 A8 | 6/2013 |

OTHER PUBLICATIONS

Shimomura, et al., "Properties and Reaction Mechanism of the Bioluminescence System of the Deep-Sea Shrimp *Oplophorus gracilorostris*," Biochemistry, 1978: vol. 17, No. 6, pp. 994-998.

Inoue, et al., "The Use of luciferase of luminous shrimp *Oplophorus gracilorostris*: cDNA of a novel imidazopyrazinone luciferase", FEBS Lett., 2000, 481 pp. 19-25.

Inoue, et al., "Soluble protein expression in *E. coli* cells using lg-G-binding domain of protein A as a solubilizing partner in the cold induced system", Biochem. Biophys. Res. Commun., 2008, 376, pp. 448-453.

Hall, et al., "Engineered Luciferase Reporter from a Deep Sea Shrimp Utilizing a Novel Imidazopyrazinone Substrate", ACS Chem. Biol., 2012, 7: pp. 1848-1857.

Inoue, et al., "The Use of *Renilla* Luciferase, *Oplophorus* Luciferase, and Apoaequorin as Bioluminescent Reporter Protein in the Presence of Coelenterazine Analogues as Substrate", Biochem. Biophys. Res. Commun., 1997, 233, pp. 349-353.

Nakamura et al., "Efficient Bioluminescence of Bisdeoxycoeienterazine with the Luciferase of a Deep Sea Shrimp *Oplophorus*", Tetrahedron Lett., 1997, vol. 38, No. 6, pp. 6405-6406.

Wu, et al., "Chemi- and bioluminescence of coelenterazine analogues with a conjugated group at the C-8 position", Tetrahedron Lett., 2001, 42, pp. 2997-3000.

Inoue, et al., "Overexpression, purification and characterization of the catalytic component of *Oplophorus* luciferase in the deep-sea shrimp, *Oplophorus gracilirostris*", Protein Express. Purif., 2007, 56, pp. 261-628.

Inoue et al., "Expression, purification and luminescence properties of coelenterazine-utilizing luciferases from *Renilla*, *Oplophorus* and *Gaussia*: Comparison of substrate specificity for C2-modified coelenterazines", Protein Express. Purif., 2013, 88, pp. 150-156.

Search Report mailed Nov. 12, 2014 in GB Application No. 1403374.0.

Search Report mailed Jun. 25, 2015 in GB Application No. 1418471.7.

Satoshi Inouye, et al., "C6-Deoxy coelenterazine analogues as an efficient substrate for glow luminescence reaction of nanoKAZ: The mutated catalytic 19 kDa component of Oplophorus luciferase," Biochemical and Biophysical Research Communications 437 (2013), pp. 23-28.

(Continued)

*Primary Examiner* — Tekchand Saidha
(74) *Attorney, Agent, or Firm* — Drinker Biddle & Reath LLP

(57) ABSTRACT

There has been a demand for a codon-optimized gene for the mutated catalytic domain of *Oplophorus* luciferase, which is capable of efficiently expressing a protein both in a cultured animal cell and *Escherichia coli*. There has also been a demand for a substrate coelenterazine analogue showing a higher activity than that of native 19 kDa protein. The invention provides a polynucleotide comprising a polynucleotide consisting of the nucleotide sequence of SEQ ID NO: 2. According to the invention, bis-coelenterazine is used as a substrate coelenterazine analogue suitable for the photoprotein encoded by the polynucleotide comprising the polynucleotide consisting of the nucleotide sequence of SEQ ID NO: 2.

11 Claims, 6 Drawing Sheets

(56) References Cited

OTHER PUBLICATIONS

Shimomura et al., "Recombinant aequorin and recombinant semi-synthetic aequorins," Biochem. J., 1990, vol. 270, pp. 309-312.
Shimomora, et al., "Semi-synthetic aequroin, An improved tool for the measurement of calcium ion concentration," Biochem. J., 1988, vol. 251, pp. 405-410.
Shimonura et al., "Semi-synthetic aequorins with improved sensitivity to Ca2+ ions," Biochem. J., 1989, vol. 261, pp. 913-920.
Katsuhori Teranishi, "Luminescence of imidazo[1,2-a]pyrazin-3(7H)-one compounds," Bioorganic Chemistry, 2007, 35, pp. 82-111.
GB Application No. 1422600.5—Search Report mailed Sep. 15, 2015.
Inouye, et al., "Unconventional secretion of the mutated 19 kDA protein of *Oplophorus luciferase* (nanoKAZ) in mammalian cells", Biochemical and Biophysical Research Communications, Jul. 11, 2014, vol. 450, , No. 4, pp. 1313-1319.
GB Application No. 1406130.3—Search Report mailed Nov. 11, 2014.
Inoye, et al., "Codon optimization of genes for efficient protein expression in mammalian cells by selection of only preferred human codons", Protein Expr. Purif., 2015, 109, pp. 47-54.

* cited by examiner

CODON-OPTIMIZED GENE FOR MUTATED SHRIMP LUCIFERASE AND METHOD FOR USE THEREOF

The priority application, Japanese patent application no. 2013-038350, filed on Feb. 28, 2013, is incorporated by reference herein in its entirety.

SEQUENCE LISTING

The instant application contains a sequence listing which has been submitted in ASCII format via EFS-Web and is hereby incorporated by reference in its entirety. Said ASCII copy, created on Feb. 19, 2014 is named G13_0077US.txt and is 31,919 bytes in size.

TECHNICAL FIELD

The present invention relates to a codon-optimized gene for the mutated catalytic domain of shrimp luciferase (*Oplophorus* luciferase), a method for use thereof, and so on.

BACKGROUND ART

The simplest light-emitting system among luciferases is performed by the luminescence reaction only with a luciferin and molecular oxygen, and a representative light-emitting system utilizes coelenterazine as a light-emitting substrate. Since the luminescence reaction is simple, a reporter assay using the gene has been widely used. Among luciferases used in the light-emitting system that utilizes coelenterazine as a substrate, *Oplophorus* luciferase, *Gaussia* luciferase and the like are known as secreted luciferases.

*Oplophorus* luciferase was isolated from the deep-sea shrimp that is classified in crustaceans and the protein was identified by Shimomura, et al. in 1978 (Non-Patent Document 1). In 2000, Inouye et al. revealed by isolation of the gene that *Oplophorus* luciferase is a complex composed of 35 kDa protein consisting of 320 amino acid residues and 19 kDa protein consisting of 169 amino acid residues (Patent Document 1, Non-Patent Document 2). It has also been demonstrated by gene expression using *Escherichia coli* and cultured animal cells that the catalytic domain responsible for the luminescent oxidation of coelenterazine is present in the 19 kDa protein (Patent Document 1, Non-Patent Document 2). When a gene encoding the 19 kDa domain protein is expressed in *Escherichia coli*, it is expressed as inclusion bodies over 95%. It is reported that the 19 kDa protein is expressed as a soluble form in the *Escherichia coli* system using the fusion protein with protein A derived ZZ-domain (Non-Patent Document 3). On the other hand, it is shown that cultured animal cells do not secret the 19 kDa protein by their own signal peptide sequence for secretion but the 19 kDa protein have a luminescence activity in the cells (Non-Patent Document 2). In 2012, a method of conventional random mutagenesis was applied to this gene of the 19 kDa domain protein to produce the mutagenized 19 kDa domain gene, which was shown to provide higher activity than that of native 19 kDa protein, named "nanoLuc." NanoLuc shows the difference of 16 amino acid residues with the native 19 kDa protein, which consists of 169 amino acid residues (KAZ), indicating 90.5% identity (Non-Patent Document 4). However, the essential amino acid residues for luminescnece function are not identified and the function of mutated amino acid residues remains unclear. Patent Document 2 discloses the mutated 19 kDa protein including nanoLuc, which shows higher activity than that of native 19 kDa protein.

Coelenterazine, a light-emitting substrate, is also known as a light-emitting substrate for *Renilla* luciferase of *Renilla reniformis* or as a source of light emission for the photoprotein aequorin isolated from *Aequorea victoria* and is a compound having an imidazopyrazinone ring as a core structure. The mechanism of light emission is considered as follows. Molecular oxygen attaches to coelenterazine and the resulting peroxide produces the dioxetanone. Subsequently, decarboxylation proceeds to form the coelenteramide anion at the excited state, which is supposed to be a light emitter. And when the anion relaxes to the ground state, it is considered to produce light emission of blue ($\lambda$max=460-490 nm). More than 50 coelenterazine analogues have been synthesized so far and luminescence properties have been investigated by using them as substrates. In particular, *Oplophorus* luciferase has a broad range of substrate specificity compared to other coelenterazine-type luciferases. It is difficult to find out coelenterazine analogues showing the luminescence activity with at least 5-fold higher than that of coelenterazine (Non-Patent Documents 5-9).

PRIOR ART DOCUMENTS

Patent Documents

[Patent Document 1] Japanese Patent No. 4613441
[Patent Document 2] Japanese Laid-Open Patent Publication No. 2012-525819

Non-Patent Documents

[Non-Patent Document 1] Shimomura O. et al. Biochemistry. 1978; 17: 994-998.
[Non-Patent Document 2] Inouye S. et al. FEBS Lett. 2000; 481: 19-25.
[Non-Patent Document 3] Inouye S. & Sahara Y. Biochem. Biophys. Res. Commun. 2008; 376: 448-53.
[Non-Patent Document 4] Hall M. P. et al. ACS Chem. Biol. 2012; 7: 1848-1857.
[Non-Patent Document 5] Inouye S. & Shimomura O. Biochem. Biophys. Res. Commun. 1997; 233: 349-353.
[Non-Patent Document 6] Nakamura, H. et al. Tetrahedron Lett. 1997; 38: 6405-6406.
[Non-Patent Document 7] Wu C. et al. Tetrahedron Lett. 2001; 42: 2997-3000.
[Non-Patent Document 8] Inouye S. & Sasaki S. Protein Express. Purif. 2007; 56: 261-268.
[Non-Patent Document 9] Inouye S. et al. Protein Express. Purif. 2013; 88: 150-156.

DISCLOSURE OF THE INVENTION

Problems to be Solved by the Invention

Coelenterazine serves as a common light-emitting substrate for various luciferases derived from marine bioluminescent organisms. However significant homology in the primary structure is not observed among these luciferases. Moreover, the catalytic domain is not clarified among them. It is thus impossible to apply a precise molecular design to the light-emitting substrate or luciferase protein and predict an optimized luciferin for these luciferases. In order to find out suitable substrates for individual luciferases, it is required to screen coelenterazine analogues and select an optimized one therefrom.

Under the foregoing circumstances, it is desired to provide a codon-optimized gene for the mutated catalytic domain of

*Oplophorus* luciferase which is capable of efficiently expressing the protein both in cultured animal cells and *Escherichia coli*. It is also desired to provide a substrate coelenterazine analogue optimized for the mutated 19 kDa protein, which is designed to show higher activity than that of native 19 kDa protein.

Means for Solving the Problems

In view of the foregoing circumstances, the inventors made diligent investigations. As a result, the inventors have found a gene encoding the mutated catalytic 19 kDa domain of codon-optimized *Oplophorus* luciferase which is capable of efficiently expressing the protein in cultured animal cells and *Escherichia coli*. Furthermore, they have screened the existing coelenterazine analogues by using polypeptides encoded the gene for luciferase enzyme as a sources and found coelenterazine analogues having high activity. The present invention has thus been accomplished bythese insights.

More specifically, the present invention provides polynucleotides, recombinant vectors, transformants, methods of producing polypeptides, kits, light-emitting methods, and so on, which are described below.

[1] A polynucleotide selected from the group consisting of (a) to (d) below:
(a) a polynucleotide comprising a polynucleotide consisting of the nucleotide sequence of SEQ ID NO: 2;
(b) a polynucleotide comprising a polynucleotide encoding a protein consisting of a nucleotide sequence in which one or more nucleotides are deleted, substituted, inserted and/or added in the nucleotide sequence of SEQ ID NO: 2, and having a luminescent catalyst activity by using luciferin as a substrate;
(c) a polynucleotide comprising a polynucleotide encoding a protein consisting of a nucleotide sequence having at least 90% identity to the nucleotide sequence of SEQ ID NO: 2, and having a luminescent catalyst activity by using luciferin as a substrate; and,
(d) a polynucleotide comprising a polynucleotide encoding a protein which hybridizes to a polynucleotide consisting of a nucleotide sequence complementary to the nucleotide sequence of SEQ ID NO: 2 under stringent conditions, and has a luminescent catalyst activity by using luciferin as a substrate.

[2] The polynucleotide according to [1] above, which is selected from the group consisting of (a) to (d) below:
(a) a polynucleotide comprising a polynucleotide consisting of the nucleotide sequence of SEQ ID NO: 2;
(b) a polynucleotide comprising a polynucleotide encoding a protein consisting of a nucleotide sequence in which 1 to 20 nucleotides are deleted, substituted, inserted and/or added in the nucleotide sequence of SEQ ID NO: 2, and having a luminescent catalyst activity by using luciferin as a substrate;
(c) a polynucleotide comprising a polynucleotide encoding a protein consisting of a nucleotide sequence having at least 95% identity to the nucleotide sequence of SEQ ID NO: 2, and having a luminescent catalyst activity by using luciferin as a substrate; and,
(d) a polynucleotide comprising a polynucleotide encoding a protein which hybridizes to a polynucleotide consisting of a nucleotide sequence complementary to the nucleotide sequence of SEQ ID NO: 2 under high stringent conditions, and has a luminescent catalyst activity by using luciferin as a substrate.

[3] The polynucleotide according to [1] above, which is selected from the group consisting of (a) to (c) below:
(a) a polynucleotide comprising a polynucleotide consisting of the nucleotide sequence of SEQ ID NO: 2;
(b) a polynucleotide comprising a polynucleotide encoding a protein consisting of a nucleotide sequence in which 1 to 10 nucleotides are deleted, substituted, inserted and/or added in the nucleotide sequence of SEQ ID NO: 2, and having a luminescent catalyst activity by using luciferin as a substrate; and,
(c) a polynucleotide comprising a polynucleotide encoding a protein consisting of a nucleotide sequence having at least 98% identity to the nucleotide sequence of SEQ ID NO: 2, and having a luminescent catalyst activity by using luciferin as a substrate.

[4] A polynucleotide comprising a polynucleotide consisting of the nucleotide sequence of SEQ ID NO: 2.

[5] The polynucleotide according to any one of [1] to [4] above, further comprising a polynucleotide encoding a polypeptide consisting of an amino acid sequence for promoting translation and/or a polynucleotide encoding a polypeptide consisting of an amino acid sequence for purification.

[6] The polynucleotide consisting of any one of the nucleotide sequences of SEQ ID NO: 5, SEQ ID NO: 8, SEQ ID NO: 10 and SEQ ID NO: 14.

[7] A recombinant vector comprising the polynucleotide according to any one of [1] to [6] above.

[8] A transformant in which the recombinant vector according to [7] above is introduced.

[9] A method of producing a protein, which comprises the step of culturing the transformant according to [8] above to produce a protein encoded by the polynucleotide according to any one of [1] to [6] above.

[10] A kit comprising the polynucleotide according to any one of [1] to [6] above, the recombinant vector according to [7] above or the transformant according to [8] above.

[11] The kit according to [10] above, further comprising bis-coelenterazine.

[12] A kit comprising:
(i) a protein encoded by the polynucleotide according to any one of [1] to [6] above; and,
(ii) bis-coelenterazine.

[13] A kit comprising:
(i) a protein selected from the group consisting of (a) to (c) below:
(a) a protein comprising the amino acid sequence of SEQ ID NO: 1;
(b) a protein comprising an amino acid sequence in which 1 to 8 amino acids are deleted, substituted, inserted and/or added in the amino acid sequence of SEQ ID NO: 1, and having a luminescent catalyst activity by using luciferin as a substrate; and,
(c) a protein comprising an amino acid sequence having at least 95% identity to the amino acid sequence of SEQ ID NO: 1, and having a luminescent catalyst activity by using luciferin as a substrate; and,
(ii) bis-coelenterazine.

[14] A method for performing a luminescence reaction, which comprises contacting a protein encoded by the polynucleotide according to any one of [1] to [6] above with bis-coelenterazine.

[15] A method for performing a luminescence reaction, which comprises contacting:
(i) a protein selected from the group consisting of (a) to (c) below:
(a) a protein comprising the amino acid sequence of SEQ ID NO: 1;
(b) a protein comprising an amino acid sequence in which 1 to 8 amino acids are deleted, substituted, inserted and/or added in the amino acid sequence of SEQ ID NO: 1, and having a luminescent catalyst activity by using luciferin as a substrate; and, (c) a protein comprising an amino acid sequence having at least 95% identity to the amino acid sequence of SEQ ID NO: 1, and having a luminescent catalyst activity by using luciferin as a substrate;
with,
(ii) bis-coelenterazine.

[16] A method for determining the activity of a sequence associated with promoter control, which comprises using as a reporter gene the polynucleotide according to any one of [1] to [6] above.

[17] The method according to [16] above, wherein bis-coelenterazine is used as a luminescent substrate.

Effects of the Invention

The present invention provides a codon-optimized gene for the mutated catalytic domain of *Oplophorus* luciferase which can efficiently express the protein in both cultured animal cells and *Escherichia coli* cells. The present invention also provides a light-emitting method which is performed by a substrate coelenterazine analogue optimized for the mutated 19 kDa protein, which shows a higher activity than that of the native 19 kDa protein.

BEST MODE FOR CARRYING OUT THE INVENTION

Figure 1:
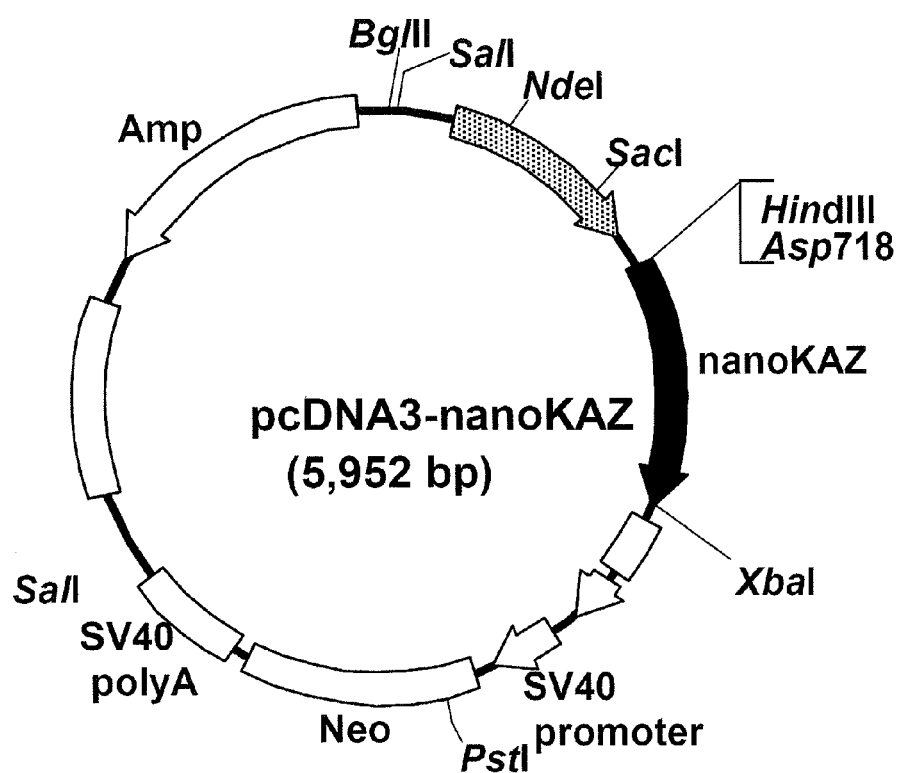
FIG. 1 shows the plasmid map of the vector pcDNA3-nanoKAZ for secretion and expression of the codon-optimized nanoKAZ domain protein without using a secretory signal peptide.

The present invention will be described below in detail.
1. Protein of the Invention The protein of the present invention is a protein comprising the amino acid sequence of a polypeptide having substantially the same activity as the protein comprising the amino acid sequence of SEQ ID NO: 1.

The term "substantially the same activity as the protein comprising the amino acid sequence of SEQ ID NO: 1" is used to mean, for example, the luminescence catalytic activity using luciferin as a substrate (herein sometimes merely referred to as "luminescence activity"), that is, the activity of catalyzing a reaction in which a luciferin (e.g., a coelenterazine analogue) is oxidized by oxygen molecules to form oxyluciferin in the excited state. The oxyluciferin formed in the excited state emits visible light and turns to the ground state.

The activity or function as described above can be determined by the method described in, e.g., Inouye, S. & Shimomura, O, (1997) Biochem, Biophys, Res. Commun. 233, 349-353. Specifically, the protein of the present invention mixes with a luciferin to start the luminescence reaction and the catalytic activity and then the luminescence can be determined by a luminometer. As the luminometer, there may be used luminometers commercially available, e.g., Luminescencer-PSN AB2200 (manufactured by Atto Co.) or Centro 960 Luminometer (manufactured by Berthoid).

The luciferin used in the present invention may be any luciferin as far as it serves as a substrate for the protein of the present invention. Specifically, the luciferin used in the present invention includes coelenterazine analogues in which the imidazopyrazinone ring is the basic skeleton.

As used herein, the coelenterazine analogue means coelenterazine and analogues thereof. Examples of the coelenterazine analogues include bis-coelenterazine, deoxy-furane-coelenterazine (furimazine), h-coelenterazine, hcp-coelenterazine, cp-coelenterazine, f-coelenterazine, fcp-coelenterazine, n-coelenterazine, MeO-coelenterazine, e-coelenterazine, cl-coelenterazine, ch-coelenterazine, 3 iso-coelenterazine, 3meo-coelenterazine, cf3-coelenterazine, i-coelenterazine, et-coelenterazine, me-coelenterazine, 3me-coelenterazine, αmeh-coelenterazine 8-(1-naphthyl)-coelenterazine, 8-(2-naphthyl)-coelenterazine, 8-(2-thienyl)-coelenterazine, 6,8-di(2-thienyl)-coelenterazine, 8-(4-hydroxyphenyl)-coelenterazine, 8-(2-benzothienyl)-coelenterazine, 8-(b-styryl)-coelenterazine, 8-phenyl-coelenterazine, 6-deoxy-coelenterazine, 8-(3-thienyl)-coelenterazine and 8-(3-benzo[b] thienyl)-coelenterazine. Of these coelenterazine analogues, bis-coelenterazine is particularly preferred in the present invention.

These coelenterazine analogues may be synthesized by publicly known methods or may also be commercially available.

The coelenterazine analogues may be synthesized by the methods described in, e.g., Shimomura et al, (1988) Biochem, J. 251, 405-410, Shimomura et al. (1989) Biochem. J. 261, 913-920, Shimomura et. al. (1990) Biochem. J. 270, 309-312, Nakamura et al, (1997) Tetrahedron Lett. 38: 6405-6406, WO 2010/090319 pamphlet, or Inouye et al. (2010) Anal. Biochem, 407, 247-252, or modifications thereof. Furimazine may be synthesized by the method described in Hall et al, (2012) ACS Chem. Biol. 16; 1848-1857.

The coelenterazine analogues which are commercially available include, for example, cf3-coelenterazine and h-coelenterazine which are coelenterazines manufactured by JNC Corp.; hcp-coelenterazine, cp-coelenterazine, f-coelenterazine, fcp-coelenterazine and n-coelenterazine manufactured by Biotium, Inc.; as well as coelenterazine, furimazine and h-coelenterazine manufactured by Promega Corp.

The term "luminescent catalyst activity by using luciferin as a substrate" preferably refers to a luminescent catalyst activity by using the coelenterazine analogue as a substrate. The term "luminescent catalyst activity by using the coelenterazine analogue as a substrate" preferably refers to a luminescent catalyst activity by using bis-coelenterazine as a substrate. The term "luminescent catalyst activity by using bis-coelenterazine as a substrate" more preferably refers to a luminescent catalyst activity which exhibits the maximum intensity of luminescence of at least 10-fold higher than that of coelenterazine when bis-coelenterazine is used as the substrate, and particularly preferably, a catalytic activity for luminescence which exhibits the maximum intensity of luminescence of at least 10-fold higher than that coelenterazine and emits light continuously when bis-coelenterazine is used as a substrate. The term "at least 10-fold higher" in the relative maximum intensity of luminescence means e.g., 10- to 20-fold, 10- to 15-fold, 10- to 14-fold, 10- to 13-fold, 10- to 12-fold or 10- to 11-fold. The continuous light-emitting time in the term "emits light continuously" means 1 minute to 120 minutes, 1 minute to 60 minutes, 1 minute to 30 minutes, 1 minute to 15 minutes, 1 minute to 10 minutes, 1 minute to 5 minutes or 1 minute to 3 minutes.

The term "protein comprising the amino acid sequence of a polypeptide having substantially the same activity as the protein comprising the amino acid sequence of SEQ ID NO: 1" is a protein selected from the group consisting of, e.g., (a) to (c) below.

(a) a protein comprising the amino acid sequence of SEQ ID NO: 1;

(b) a protein comprising an amino acid sequence in which 1 to 8 amino acids are deleted, substituted, inserted and/or added in the amino acid sequence of SEQ ID NO: 1, and having a luminescent catalyst activity by using luciferin as a substrate; and, (c) a protein comprising an amino acid sequence having at least 95% identity to the amino acid sequence of SEQ ID NO: 1, and having a luminescent catalyst activity by using luciferin as a substrate; and, As used herein, the term "1 to 8 amino acids are deleted, substituted, inserted and/or added" means that 1 to 8 amino acid residues are deleted, substituted, inserted and/or added at an optional position(s) in the same sequence and at a position(s) in the 1 to 8 amino acid sequences.

The term "1 to 8" in the "amino acid sequence in which 1 to 8 amino acids are deleted, substituted, inserted and/or added" means the range of, e.g., 1 to 8, 1 to 7, 1 to 6 (1 to several), 1 to 5, 1 to 4, 1 to 3, 1 to 2 or 1. The less the number of amino acids which are deleted, substituted, inserted or added, the more preferable. In the deletion, substitution, insertion and addition of the amino acid residues described above, two or more may occur concurrently. Such domains can be acquired using the site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

Examples of amino acid residues which are mutually substitutable are provided below. Amino acid residues in the same group are mutually substitutable.

Group A: leucine, isoleucine, norleucine, valine, norvaline, alanine, 2-aminobutanoic acid, methionine, o-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine; and,

Group G: phenylalanine and tyrosine.

In the amino acid sequence in which 1 to 8 amino acids are deleted, substituted, inserted and/or added in the amino acid sequence of SEQ ID NO: 1, it is preferred that all of the amino acids of 6th Glu, 13th Arg, 20th Leu, 29th Leu, 35th Asn, 45th Arg, 46th Ile, 56th Ile, 70th Asp, 74th Gln, 77th Lys, 92nd Val, 117th Glu, 126th Lys, 140th Ile and 168th Arg are not deleted or substituted in the amino acid sequence of SEQ ID NO: 1.

As used herein, the range of "at least 95%" in the "amino acid sequence having at least 95% identity" means, e.g., at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In general, the larger identity percentage described above is the more preferable. The identity between amino acid sequences or nucleotide sequences can be determined by using a sequencing program such as BLAST (see, e.g., Altzchul, S. F. et al., J. Mol. Biol., 215, 403 (1990), etc.) or the like. When BLAST is used, the default parameters for the respective programs are employed.

Furthermore, the protein of the present invention may be a protein encoded by the polynucleotide of the present invention later described.

Preferably, the protein of the present invention is a protein selected from the group consisting of (a) to (c) below.

(a) a protein comprising the amino acid sequence of SEQ ID NO: 1;

(b) a protein comprising an amino acid sequence in which 1 to 4 amino acids are deleted, substituted, inserted and/or added in the amino acid sequence of SEQ ID NO: 1, and having a luminescent catalyst activity by using luciferin as a substrate; and, (c) a protein comprising an amino acid sequence having at least 98% identity to the amino acid sequence of SEQ ID NO: 1, and having a luminescent catalyst activity by using luciferin as a substrate.

More preferably, the protein of the present invention is a protein comprising the polypeptide consisting of the amino acid sequence of SEQ ID NO: 1.

The protein of the present invention may further contain an additional peptide sequence at the N terminus and/or C terminus, preferably at the N terminus. The additional peptide sequence includes, for example, at least one peptide sequence selected from the group consisting of a peptide sequence for promoting translation, a peptide sequence for purification, a signal peptide sequence for secretion, a peptide sequence for expressing the protein of the present invention as a soluble protein and an epitope sequence capable of recognizing an antibody. The additional peptide sequence is preferably a peptide sequence for purification and/or a signal peptide sequence for secretion. In another preferred embodiment of the present invention, the additional peptide sequence is at least one sequence selected from the group consisting of a peptide sequence for purification, a signal peptide sequence for secretion and a sequence for expressing the protein of the present invention as a soluble protein.

The fusion protein of the present invention may further contain a linker sequence for restriction enzyme site.

Peptide sequences used in the art may be employed as the peptide sequence for promoting translation. The peptide sequence for promoting translation includes, for example, a TEE sequence.

Peptide sequences employed in the art can be used as the peptide sequence for purification. The peptide sequence for purification includes, for example, a histidine tag sequence having an amino acid sequence of at least 4, preferably at least 6 consecutive histidine residues, an amino acid sequence with a binding domain of glutathione S-transferase into glutathione, the amino acid sequence of Protein A and an avidin tag sequence, etc.

The secretory signal peptide means a peptide region which has the role of transporting a protein bound to the secretory signal peptide across a cell membrane. Amino acid sequences of such secretory signal peptides and nucleic acid sequences encoding the same are well known in the art and reported (see, e.g., von Heijine G. (1988) Biochim. Biohys. Acta 947: 307-333, von Heijine G (1990) J. Membr. Biol. 115: 195-201). Specific examples of the secretory signal peptide include the secretory signal peptide from the outer membrane protein A of *Escherichia coli* (OmpA) (Ghrayeb, J. et al., (1984) EMBO J. 3:2437-2442), the secretory signal peptide from cholera toxin obtained from *Vibrio cholerae* and the secretory signal peptide form *Gaussia* luciferase used in EXAMPLES later described.

The peptide sequence used to express the protein of the present invention as a soluble protein includes, for example, polypeptides represented by formula (Z)n (ZZ domain in particular). The amino acid sequences for the polypeptides represented by formula (Z)n and the nucleic acid sequences encoding the same are described in, e.g., Japanese Laid-Open Patent Publication No. 2008-99669.

As the linker sequences for restriction enzyme sites, peptide sequences used in the art can be employed.

In some embodiments of the present invention, the protein is a protein comprising the polypeptide consisting of any one of the amino acid sequences of SEQ ID NO: 6, SEQ ID NO: 7, SEQ ID NO: 9, SEQ ID NO: 11, SEQ ID NO: 15 and SEQ ID NO: 16.

The method for acquiring the protein of the invention is not particularly limited. The protein of the invention may be a protein synthesized by chemical synthesis, or a recombinant protein produced by genetic engineering technique. When the protein of the invention is to be chemically synthesized, synthesis may be carried out by the Fmoc (fluorenylmethyloxycarbonyl) method or the tBoc (t-butyloxycarbonyl) method. In addition, peptide synthesizers available from Advanced ChemTech, PerkinElmer, Pharmacia, Protein Technology Instrument, Synthecell-Vega, PerSeptive, Shimadzu Corporation, etc. may also be used for the chemical synthesis. When the protein of the invention is to be produced by genetic engineering technique, the protein may be produced by a conventional genetic recombination technique. More specifically, the protein of the invention may be produced by inserting a polynucleotide (e.g., a DNA) encoding the protein of the invention into a suitable expression system. The polynucleotide encoding the protein of the invention, expression of the protein of the invention in an expression system, etc. will be later described.

2. Polynucleotide of the Invention

The present invention also provides the polynucleotide encoding the protein of the invention described above. The polynucleotide of the invention may be any polynucleotide as far as it comprises a nucleotide sequence encoding the protein of the invention, and a DNA is preferred. Examples of the DNA include genomic DNA, genomic DNA library, cellular or tissue cDNA, cellular or tissue cDNA library, synthetic DNA, etc. Vectors used in the libraries are not particularly limited and may be any of bacteriophages, plasmids, cosmids, phagemids, etc. Additionally, these vectors may be amplified directly by a reverse transcription polymerase chain reaction (hereinafter abbreviated as RT-PCR) using the total RNA or mRNA fraction prepared from the cell or tissue described above.

Specifically, the polynucleotide of the invention includes any polynucleotide selected from the group consisting of (a) to (d) below:
(a) a polynucleotide comprising a polynucleotide consisting of the nucleotide sequence of SEQ ID NO: 2;
(b) a polynucleotide comprising a polynucleotide encoding a protein consisting of a nucleotide sequence in which one or more nucleotides are deleted, substituted, inserted and/or added in the nucleotide sequence of SEQ ID NO: 2, and having a luminescent catalyst activity by using luciferin as a substrate;
(c) a polynucleotide comprising a polynucleotide encoding a protein consisting of a nucleotide sequence having at least 90% identity to the nucleotide sequence of SEQ ID NO: 2, and having a luminescent catalyst activity by using luciferin as a substrate; and,
(d) a polynucleotide comprising a polynucleotide encoding a protein which hybridizes to a polynucleotide consisting of a nucleotide sequence complementary to the nucleotide sequence of SEQ ID NO: 2 under stringent conditions, and has a luminescent catalyst activity by using luciferin as a substrate.

Herein, the term "luminescent catalyst activity by using luciferin as a substrate" is the same as defined above.

The term "nucleotide sequence in which one or more nucleotides are deleted, substituted, inserted and/or added" means that one or more nucleotides are deleted, substituted, inserted and/or added at an optional position(s) in the same sequence and at a position(s) in one or more nucleotide sequences.

The term "one or more" in the "nucleotide sequence in which one or more nucleotides are deleted, substituted, inserted and/or added" means the range of, e.g., 1 to 20, 1 to 15, 1 to 10, 1 to 9, 1 to 8, 1 to 7, 1 to 6 (1 to several), 1 to 5, 1 to 4, 1 to 3, 1 to 2 or 1. The less number of nucleotides which are deleted, substituted, inserted or added are the more preferable. In the deletion, substitution, insertion and addition of the nucleotides described above, two or more may occur concurrently. Such domains can be acquired by using the site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

The polynucleotide in which one or more amino acid residues are deleted, substituted, inserted and/or added in a given nucleotide sequence may be obtained by using a site-specific mutagenesis technique (cf., e.g., Gotoh, T. et al., Gene 152, 271-275 (1995), Zoller, M. J., and Smith, M., Methods Enzymol. 100, 468-500 (1983), Kramer, W. et al., Nucleic Acids Res. 12, 9441-9456 (1984), Kramer W, and Fritz H. J., Methods. Enzymol. 154, 350-367 (1987), Kunkel, T. A., Proc. Natl. Acad. Sci. USA. 82, 488-492 (1985), and Kunkel, Methods Enzymol. 85, 2763-2766 (1988)), methods using amber mutation (cf., e.g., the gapped duplex method, Nucleic Acids Res., 12, 9441-9456 (1984)).

Alternatively, a mutation may also be introduced into the polynucleotide by PCR using a set of primers bearing on each 5' end a sequence in which the target mutation (deletion, addition, substitution and/or insertion) has been introduced (cf., e.g., Ho, S, N. et al., Gene, 77, 51 (1989)).

A polynucleotide encoding a partial protein fragment, which is one type of deletion mutants, can be obtained by using as primers an oligonucleotide having a sequence which matches the nucleotide sequence at the 5' end of the region encoding the partial fragment to be produced in the polynucleotide encoding the target protein and an oligonucleotide having a sequence complementary to the nucleotide sequence at the 3' end thereof, and performing PCR in which the polynucleotide encoding the target protein serves as a template.

The range of "at least 90%" in the "nucleotide sequence having at least 90% identity" means, e.g., at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9%. In general, the larger identity percentage described above is the more preferable. The identity between amino acid sequences or nucleotide sequences can be determined by using a sequencing program such as BLAST (see, e.g., Altzchul, S. F. et al., J. Mol. Biol., 215, 403 (1990)), or the like. When BLAST is used, the default parameters for the respective programs are employed.

The term "polynucleotide which hybridizes under stringent conditions" means a polynucleotide (e.g., a DNA) which is obtained by colony hybridization, plaque hybridization, Southern blot hybridization or the like using as a probe the whole or part of the polynucleotide consisting of a nucleotide sequence complementary to the nucleotide sequence of SEQ ID NO: 2. Specifically, the polynucleotide includes a polynucleotide which can be identified by performing hybridization at 65° C. in the presence of 0.7 to 1.0 mol/L NaCl with a filter on which the DNA derived from colony or plaque is immobilized, and then washing the filter in 0.1 to 2× SSC (saline-sodium citrate) solution (1× SSC solution is composed of 150 mmol/L sodium chloride and 15 mmol/L sodium citrate) at 65° C.

Hybridization may be carried out by modifications of the methods described in laboratory manuals such as Sambrook J. et al., Molecular Cloning: A Laboratory Manual, Third Edition, Cold Spring Harbor Laboratory Press (2001), Ausbel F. M. et al., Current Protocols in Molecular Biology, Supplement 1-38, John Wiley and Sons (1987-1997), Glover D. M. and Hames B. D., DNA Cloning 1: Core Techniques, A practical Approach, Second Edition, Oxford University Press (1995), etc.

The term "stringent conditions" may be any of low stringent conditions, moderate stringent conditions and high stringent conditions. The "low stringent conditions" are, for example, 5× SSC, 5× Denhardt's solution, 0.5% (w/v) SDS, 50% (v/v) formamide and 32° C. The "moderate stringent conditions" are, for example, 5× SSC, 5× Denhardt's solution, 0.5% (w/v) SDS, 50% (v/v) formamide and 42° C. The "high stringent conditions" are, for example, 5× SSC, 5× Denhardt's solution, 0.5 (w/v) % SDS, 50% (v/v) formamide and 50° C. As the conditions are severer, complementation required for duplex formation is higher. Specifically, under these conditions, for example, as the temperature is higher, a polynucleotide (e.g., a DNA) with higher homology is expected to be obtained efficiently. Provided that multiple factors are involved in the hybridization stringency including temperature, probe concentration, probe length, ionic strength, time, salt concentration and the like, those skilled in the art may achieve similar stringency by appropriately choosing these factors.

When a commercially available kit is used for hybridization, for example, Alkphos Direct Labeling Reagents (manufactured by Amersham Pharmacia) can be used. In this case, according to the protocol attached, a membrane is incubated with a labeled probe overnight, the membrane is washed with a primary wash buffer containing 0.1% (w/v) SDS at 55° C. and then the hybridized DNA can be detected.

Other hybridizable polynucleotides include, as calculated by sequencing programs such as BLAST or the like by using the default parameters, DNAs with identity of approximately 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8% or more, or 99.9% or more, to the polynucleotide encoding the polynucleotide consisting of the nucleotide sequence of SEQ ID NO: 2.

The identity of nucleotide sequences can be determined by using the method described above.

In a preferred embodiment of the present invention, the polynucleotide is a polynucleotide selected from the group consisting of (a) to (d) below:

(a) a polynucleotide comprising a polynucleotide consisting of the nucleotide sequence of SEQ ID NO: 2;

(b) a polynucleotide comprising a polynucleotide encoding a protein consisting of a nucleotide sequence in which 1 to 20 nucleotides are deleted, substituted, inserted and/or added in the nucleotide sequence of SEQ ID NO: 2, and having a luminescent catalyst activity by using luciferin as a substrate;

(c) a polynucleotide comprising a polynucleotide encoding a protein consisting of a nucleotide sequence having at least 95% identity to the nucleotide sequence of SEQ ID NO: 2, and having a luminescent catalyst activity by using luciferin as a substrate; and, (d) a polynucleotide comprising a polynucleotide encoding a protein which hybridizes to a polynucleotide consisting of a nucleotide sequence complementary to the nucleotide sequence of SEQ ID NO: 2 under high stringent conditions, and has a luminescent catalyst activity by using luciferin as a substrate.

In a more preferred embodiment of the invention, the polynucleotide is a polynucleotide selected from the group consisting of (a) to (c) below:

(a) a polynucleotide comprising a polynucleotide consisting of the nucleotide sequence of SEQ ID NO: 2;

(b) a polynucleotide comprising a polynucleotide encoding a protein consisting of a nucleotide sequence in which 1 to 10 nucleotides are deleted, substituted, inserted and/or added in the nucleotide sequence of SEQ ID NO: 2, and having a luminescent catalyst activity by using luciferin as a substrate; and, (c) a polynucleotide comprising a polynucleotide encoding a protein consisting of a nucleotide sequence having at least 98% identity to the nucleotide sequence of SEQ ID NO: 2, and having a luminescent catalyst activity by using luciferin as a substrate.

In a particularly preferred embodiment of the invention, the polynucleotide is a polynucleotide comprising a polynucleotide consisting of the nucleotide sequence of SEQ ID NO: 2.

The polynucleotide of the present invention may further contain a polynucleotide comprising a polynucleotide encoding an additional peptide sequence. The additional peptide sequence includes, for example, at least one peptide sequence selected from the group consisting of a peptide sequence for promoting translation, a peptide sequence for purification, a signal peptide sequence for secretion, a peptide sequence for expressing the fusion protein of the present invention as a soluble protein and an epitope sequence capable of recognizing an antibody.

The polynucleotide of the present invention may further contain a polynucleotide encoding a linker sequence for restriction enzyme sites.

Polynucleotides comprising polynucleotides encoding the peptide sequences used in the art may be employed as the polynucleotide comprising a polynucleotide encoding the peptide sequence for promoting translation. Examples of the peptide sequence for promoting translation include those described above.

Polynucleotides comprising nucleotide sequences encoding peptide sequences used in the art may be employed as the polynucleotide encoding the peptide sequence for purification. Examples of the peptide sequence for purification include those described above.

Polynucleotides comprising nucleic acid sequences encoding secretory signal peptides known in the art may be used as the polynucleotide encoding a secretory signal peptide. Examples of the secretory signal peptide include those described above.

Polynucleotides comprising nucleic acid sequences encoding peptides for expressing as a soluble protein known in the art may be used as the polynucleotide encoding a peptide sequence for expressing the protein of the invention as a soluble protein. Examples of the peptide for expressing the protein of the invention as a soluble protein include those described above.

Polynucleotides comprising nucleotide sequences encoding peptide sequences for purification known in the art may be used as the polynucleotide encoding linker sequences for restriction enzyme sites.

In some embodiments of the present invention, the polynucleotide is a polynucleotide comprising the polynucleotide consisting of any one of the nucleotide sequences of SEQ ID NO: 5, SEQ ID NO: 8, SEQ ID NO: 10 and SEQ ID NO: 14.

3. Recombinant Vector and Transformant of the Invention

The present invention further provides recombinant vectors and transformants comprising the polynucleotides of the present invention described above.

Preparation of Recombinant Vector

The recombinant vector of the invention can be obtained by ligating (inserting) the polynucleotide (DNA) of the invention to (into) an appropriate vector. More specifically, the recombinant vector can be obtained by digesting the purified polynucleotide (DNA) with a suitable restriction enzyme, then inserting into a suitable vector at the restriction enzyme site or multicloning site, and ligating to the vector. The vector for inserting the polynucleotide of the invention is not particularly limited as far as it is replicable in a host. Vectors which may be used for this purpose include plasmids, bacteriophages, animal viruses, etc. Examples of plasmids include plasmids from *Escherichia coli* (e.g., pBR322, pBR325, pUC118, pUC119, etc.), plasmids from *Bacillus subtilis* (e.g., pUB110, pTP5, etc.), and plasmids from yeast (e.g., YEp13, YEp24, YCp50, etc.). Examples of bacteriophages include k phage, etc. Examples of animal viruses include retroviruses, vaccinia viruses and insect viruses (e.g., baculoviruses). In addition, the pCold I vector, pCold II vector, pCold III vector and pCold IV vector (all are manufactured by Takara-Bio), the PICZ a vector (manufactured by Invitrogen) and the like can also be suitably used.

The polynucleotide of the present invention is generally ligated in an expressible manner downstream from a promoter in a suitable vector. When the host used for transformation is an animal cell, the promoter is preferably an SV40-derived promoter, retrovirus promoter, metallothionein promoter, heat shock promoter, cytomegalovirus promoter, SRa promoter, and so on. When the host is a bacterium of the genus *Escherichia*, Trp promoter, T7 promoter, lac promoter, recA promoter, λPL promoter, lpp promoter, etc. are preferred. When the host is a bacterium of the genus *Bacillus*, SPO1 promoter, SPO2 promoter, penP promoter, etc. are preferred. When the host is yeast, PHO5 promoter, PGK promoter, GAP promoter, ADH1 promoter, GAL promoter, etc. are preferred. When the host is an insect cell, polyhedrin promoter, P10 promoter, etc. are preferred.

A low-temperature expression-inducible promoter may also be suitably used. The low-temperature expression-inducible promoter includes, for example, a promoter sequence for cold shock gene. The cold shock gene includes, for example, *Escherichia coli* cold shock genes (e.g., cspA, cspB, cspG, cspI and csdA), *Bacillus caldolyticus* cold shock genes (e.g., Bc-Csp), *Salmonella enterica* cold shock genes (e.g., cspE), and *Erwinia carotovora* cold shock genes (e.g., cspG). Among others, cspA promoter, cspB promoter, cspG promoter, cspI promoter, csdA promoter and the like can be suitably used as the low-temperature expression-inducible promoter.

In addition to the foregoing, the recombinant vector of the invention may further contain, optionally, an enhancer, a splicing signal, a polyA addition signal, a ribosome binding sequence (SD sequence), a selection marker, etc., and provided for use. The selection marker includes, for example, a dihydrofolate reductase gene, an ampicillin resistance gene and a neomycin resistance gene.

Preparation of Transformant

The obtained recombinant vector comprising the polynucleotide of the invention (i.e., the polynucleotide encoding the protein of the invention) is introduced into an appropriate host, and the transformant can be prepared. The host is not particularly limited as far as it is capable of expressing the polynucleotide (DNA) of the invention. For example, the host may be bacteria of the genera *Escherichia*, *Bacillus*, *Pseudomonas* and *Rhizobium*, yeast, animal cells or insect cells, etc. Bacteria of the genus *Escherichia* include *Escherichia coli*, etc. Bacteria of the genus *Bacillus* include *Bacillus subtilis*, etc. Bacteria of the genus *Pseudomonas* include, for example, *Pseudomonas putida*, etc. Bacteria of the genus *Rhizobium* include, for example, *Rhizobium meliloti*, etc. Yeast includes, for example, *Saccharomyces cerevisiae*, *Schizosaccharomyces pombe*, etc. Animal cells include, for example, COS cells, CHO cells, HeLa cells, etc. Insect cells include, for example, Sf9, Sf21, etc.

The method of transfecting the recombinant vector into the host and the method of transformation thereby can be performed according to various general methods. The method for transfecting the recombinant vector into the host cell includes, for example, the calcium phosphate method (Virology, 52, 456-457 (1973)), the lipofection method (Proc. Natl. Acad. Sci. USA, 84, 7413 (1987)), the electroporation method (EMBO J., 1, 841-845 (1982)), etc. The method for transformation of the bacteria of the genus *Escherichia* includes the methods described in, e.g., Proc. Natl. Acad. Sci. USA, 69, 2110 (1972), Gene, 17, 107 (1982), etc. The method for transformation of the bacteria of the genus *Bacillus* includes, for example, the method described in Molecular & General Genetics, 168, 111 (1979). The method for transformation of yeast includes, for example, the method described in Proc. Natl. Acad. Sci. USA, 75, 1929 (1978). The method for transformation of animal cells includes, for example, the method described in Virology, 52, 456 (1973). The method for transformation of insect cells includes, for example, the method described in Bio/Technology, 6, 47-55 (1988). As such, the transformant transformed with the recombinant vector comprising the polynucleotide encoding the protein of the invention (i.e., the polynucleotide of the invention) can be yielded.

Expression Vector and Transformant Comprising Low-temperature Expression-inducible Promoter Sequence Among others, the expression vector comprising the low-temperature expression-inducible promoter sequence is preferred as the expression vector.

The expression vector comprising the low-temperature expression-inducible promoter sequence refers specifically to an expression vector comprising the following promoter sequence and coding sequence:

(1) a low-temperature expression-inducible promoter sequence; and,
(2) a coding sequence comprising the polynucleotide of the invention.

The low-temperature expression-inducible promoter sequence means a promoter sequence which is capable of inducing expression of the protein by lowering the temperature from the culture conditions under which host cells can grow. Examples of the low-temperature expression-inducible promoter are promoters for genes which encode cold shock proteins (cold shock genes). Examples of the cold shock gene promoters include those as described above.

The temperature at which the low-temperature expression-inducible promoter used in the invention is expression-inducible is generally 30° C. or lower, preferably 25° C. or lower, more preferably 20° C. or lower, and most preferably 15° C. or lower. In order to induce the expression more efficiently, however, the expression induction is generally performed at 5° C. or higher, preferably at 10° C. or higher, and most preferably at approximately 15° C.

In case of preparing the expression vector of the invention comprising the low-temperature expression-inducible promoter sequence, the pCold I vector, pCold II vector, pCold III vector, and pCold IV vector (all manufactured by Takara-Bio) can be suitably used as the vector for insertion of the polynucleotide of the invention. The protein can be produced as a soluble protein in the cytoplasm serving as a host when expression is performed in a prokaryotic host cell using these vectors.

Prokaryotic cells are preferred as the host into which the expression vector comprising the low-temperature expression-inducible promoter sequence is introduced, *Escherichia coli* being more preferred, and the BL21 and JM109 strains being particularly preferred. Among others, the BL21 strain is most preferred.

Temperatures generally of 25° C. to 40° C. and preferably of 30° C. to 37° C. are used for cultivation temperature for bringing about cell proliferation of the transformant that has been transfected with an expression vector according to the invention that includes a low-temperature expression-inducible promoter sequence. The temperature for expression induction is usually 4° C. to 25° C., preferably 10° C. to 20° C., more preferably 12° C. to 18° C., and particularly preferably 15° C.

4. Production of Protein of the Invention

The present invention further provides a method for producing the protein of the invention, which comprises the steps of culturing the transformant described above and producing the protein of the invention. The protein of the invention can be produced, for example, by culturing the transformant described above under conditions where the polynucleotide (DNA) encoding the protein of the invention can be expressed, producing/accumulating and then separating/purifying the protein of the invention.

Incubation of Transformant

The transformant of the invention can be incubated in a conventional manner used for incubation of a host. Thereby, the protein of the invention is produced by the transformant. The protein of the invention is accumulated within the transformant or in the culture medium.

The medium for culturing the transformant using bacteria of the genus *Escherichia* or the genus *Bacillus* as a host may be any of natural media and synthetic media as far as they are media that contain carbon sources, nitrogen sources, inorganic salts, etc. necessary for growth of the transformant, and in which the transformant can efficiently grow. Examples of carbon sources which can be used are carbohydrates such as glucose, fructose, sucrose, starch, etc.; organic acids such as acetic acid, propionic acid, etc.; alcohols such as ethanol, propanol, and the like. Examples of nitrogen sources which can be used include ammonia, ammonium salts of inorganic or organic acids such as ammonium chloride, ammonium sulfate, ammonium acetate, ammonium phosphate, etc., and other nitrogen-containing compounds, and further include peptone, meat extracts, corn steep liquor, and the like. Examples of inorganic salts include monobasic potassium phosphate, dibasic potassium phosphate, magnesium phosphate, magnesium sulfate, sodium chloride, ferrous sulfate, manganese sulfate, copper sulfate, calcium carbonate, etc. If necessary, antibiotics such as ampicillin or tetracycline can be added to the medium during incubation. Where the transformant transformed by the expression vector using an inducible promoter as the promoter is cultured, an inducer may also be added to the medium, if necessary. For example, when the transformant transformed by an expression vector using a Lac promoter is cultured, isopropyl-β-D-thiogalactopyranoside (IPTG), etc. may be added to the medium and indoleacrylic acid (IAA), etc. may be added to the medium when the transformant transformed by an expression vector using a trp promoter is cultured.

When the host is bacteria of the genus *Escherichia*, incubation is performed generally at approximately 15° C. to 43° C. for approximately 3 to 24 hours. If necessary, aeration and agitation may be applied. When the host is bacteria of the genus *Bacillus*, incubation is performed generally at approximately 30° C. to 40° C. for approximately 6 to 24 hours. If necessary, aeration and agitation may be applied.

Media for incubation of the transformant when the host is yeast include, for example, Burkholder's minimal medium (Proc. Natl. Acad. Sci. USA, 77, 4505 (1980)) and an SD medium containing 0.5% (w/v) Casamino acids (Proc. Natl. Acad. Sci. USA, 81, 5330 (1984)). Preferably, the pH of the medium is adjusted to approximately 5 to 8. Incubation is performed generally at approximately 20 to 35° C. for approximately 24 to 72 hours. If necessary, aeration and agitation may be applied.

Media for culturing the transformant when the host is an animal cell include MEM medium supplemented with approximately 5 to 20% (v/v) fetal calf serum (Science, 122, 501 (1952)), DMEM medium (Virology, 8, 396 (1959)), etc. Preferably, the pH of the medium is adjusted to approximately 6 to 8. Incubation is performed generally at approximately 30 to 40° C. for approximately 15 to 60 hours. If necessary, aeration and agitation may be applied.

Media for culturing the transformant when the host is an insect cell include Grace's insect medium (Nature, 195, 788 (1962)) to which additives such as 10% (v/v) immobilized bovine serum are suitably added. Preferably, the pH of the medium is adjusted to approximately 6.2 to 6.4. Incubation is performed generally at approximately 27° C. for approximately 3 to 5 days. If necessary, aeration and agitation may be applied.

Temperature for incubation and expression induction at which the transformant is transformed by the expression vector comprising the low-temperature expression-inducible promoter sequence is the same as described above.

Separation/Purification of Protein of the Invention

The protein of the present invention can be obtained by separating/purifying the protein of the present invention from the culture described above. As used herein, the culture means any one of cultured media, cultured cells or cultured bacteria and cell lysates of the cultured cells or cultured bacteria. The protein of the present invention can be separated/purified in a conventional manner.

Specifically, when the protein of the present invention accumulates in the cultured bacteria or cultured cells, after completion of the incubation, the bacteria or cells are disrupted in a conventional manner (e.g., ultrasonication, lysozyme, or freezing and thawing) and then a crude extract of the protein of the invention can be obtained in a conventional manner (e.g., centrifugation or filtration). When the protein of the invention accumulates in the periplasmic space, after completion of the incubation, the extract containing the protein of the invention can be obtained in a conventional manner (e.g., the osmotic shock method). When the protein of the invention accumulates in the cultured media, after completion of the incubation, the culture supernatant containing the protein of the invention can be obtained by separating the bacteria or cells and the culture supernatant in a conventional manner (e.g., centrifugation or filtration).

The protein of the invention contained in the extract or culture supernatant thus obtained can be purified by conventional methods of separation and purification. Examples of these separation and purification methods which may be used include ammonium sulfate precipitation, gel filtration chromatography, ion-exchange chromatography, affinity chromatography, reversed-phase high-performance liquid chromatography, dialysis, ultrafiltration, etc., alone or in a suitable combination thereof. When the protein of the invention contains the peptide sequence for purification described above, it is preferred to perform the purification by using the same. Specifically, when the protein of the invention contains a histidine tag sequence, nickel chelate affinity chromatography may be used; when the protein of the invention contains the binding domain of S-transferase to glutathione, affinity chromatography with a glutathione-binding gel may be used; when the protein of the invention contains the amino acid sequence of Protein A, antibody affinity chromatography may be used.

5. Use of Protein of the Invention

Use as Detection Marker by Luminescence

The protein of the invention can be utilized as a detection marker which emits luminescence in the presence of a luciferin (hereinafter "detection marker of the present invention"). The detection marker of the present invention can be used to detect a target substance in, e.g., an immunoassay, a hybridization assay, etc.

The protein of the invention can be expressed, e.g., as a fusion protein with a target protein, and introduced into cells by means of the microinjection method, etc., and the resulting product can be used to determine distribution of the target protein described above. Distribution of the target protein or the like can be determined by using detection methods such as luminescence imaging. In addition to the introduction into cells by means of the microinjection method or the like, the protein of the invention can also be expressed in cells and provided for use.

The light-emitting substrates (luciferins) used are preferably coelenterazine analogues, and particularly preferably bis-coelenterazine, as described above.

Use as Reporter Protein

The protein of the invention may also be used as a reporter protein to assay the transcription activity of promoters, etc. The polynucleotide encoding the protein of the invention (i.e., the polynucleotide of the invention) is fused to a target promoter or some other expression control sequence (e.g., an enhancer) to construct a vector. By introducing the vector into a host cell and detecting the luminescence from the protein of the invention in the presence of a luciferin (light-emitting substrate), the activity of the target promoter or some other expression control sequence can be assayed.

The light-emitting substrates (luciferins) used are preferably coelenterazine analogues, as described above.

The polynucleotide of the present invention can be used as a reporter gene as described above.

Material for Amusement Supplies

The protein of the invention has the activity of catalyzing the reaction that luciferin is oxidized with oxygen molecules to form oxyluciferin in the excited state. The oxyluciferin in the excited state emits visible light and turns to the ground state. Accordingly, the protein, etc. of the invention can be used preferably as a luminescent material for amusement supplies. Examples of such amusement supplies are luminescent soap bubbles, luminescent ice bars, luminescent candies, luminescent color paints, etc. These amusement supplies can be prepared in a conventional manner.

The luciferins used are preferably coelenterazine analogues, and particularly preferably bis-coelenterazine, as described above.

Bioluminescence Resonance Energy Transfer (BRET) Method

The protein of the present invention can be used for analyses including an analysis of biological functions, an assay for enzyme activities, etc., based on the principle of intermolecular interaction by the bioluminescence resonance energy transfer (BRET) method.

For example, when the protein of the invention (sometimes referred to as "the luciferase of the invention") is used as a donor and the fluorescent substance (e.g., an organic compound, and a fluorescent protein) is used as an acceptor, the interactions between the donor and acceptor can be detected by generating bioluminescence resonance energy transfer (BRET) between them.

In an embodiment of the present invention, the organic compound used as an acceptor is Hoechst 3342, Indo-1, DAP1, etc. In another embodiment of the present invention, the fluorescent protein used as an acceptor is a green fluorescent protein (GFP), a blue fluorescent protein (BFP), a mutant GFP fluorescent protein, phycobilin, etc.

In a preferred embodiment of the present invention, the physiological functions to be analyzed include an orphan receptor (especially, a G protein-coupled receptor), apoptosis, transcription regulation by gene expression, etc. Further in a preferred embodiment of the present invention, the enzyme to be analyzed is protease, esterase, kinase, or the like.

Analysis of the physiological functions by the BRET method can be performed by known methods, for example, by modifications of the method described in Biochem. J. 2005, 385, 625-637 or Expert Opin. Ther Tarets, 2007 11: 541-556. Measurement of enzyme activities may also be performed by known methods, for example, by modifications of the method described in Nature Methods 2006, 3:165-174, or Biotechnol. J. 2008, 3:311-324.

The light-emitting substrates (luciferins) used are preferably coelenterazine analogues, and particularly preferably bis-coelenterazine, as described above.

6. Kit of the Invention

The present invention further provides a kit comprising any one selected from the polynucleotide of the invention, the recombinant vector of the invention, the transformant of the invention and the complex of the invention. The present invention also provides a kit comprising the protein of the invention. The kit of the present invention may further contain a luciferin.

The luciferins used are preferably coelenterazine analogues, and particularly preferably bis-coelenterazine, as described above.

The kit of the present invention can be prepared with conventional materials by conventional methods. The kit of the present invention may further contain, e.g., sample tubes, plates, instructions for the kit user, solutions, buffers, reagents, and samples suitable for standardization or control samples. The kit of the present invention may further contain salts including halide ions.

The kit of the present invention can be used for the aforesaid measurement using a reporter protein or a reporter gene, the analysis of physiological functions or measurement of enzyme activities by the BRET method. The kit may also be used in the method for a luminescence reaction later described.

7. Method for Luminescence Reaction

Catalytic Activity for Luminescence

The protein of the invention has the activity of catalyzing a reaction in which a luciferin (e.g., a coelenterazine analogue) is oxidized by oxygen molecules to form oxyluciferin in the excited state. The oxyluciferin in the excited state emits visible light when it turns to the ground state. Namely, the fusion protein, etc. of the present invention has the activity of catalyzing the luminescence reaction where luciferin serves as a substrate, thereby to emit light. This activity is sometimes referred to as the "catalytic activity for luminescence."

Luminescence Reaction

The luminescence reaction comprising the protein of the invention and luciferin that serves as a substrate can be performed by contacting the protein of the invention with luciferin. As used herein, the term "contact" means that the protein of the present invention and luciferin are allowed to be present in the same reaction system, and includes, for example, states that the protein of the present invention is added to a container charged with luciferin, luciferin is added to a container charged with the protein of the present invention, and the protein of the present invention is mixed with luciferin. The reaction may be performed under conditions ordinarily used for the luminescence reaction using *Oplophorus* luciferase or modifications thereof.

Specifically, solvents for the reaction which are employed include a buffer solution such as Tris-HCl buffer, sodium phosphate buffer, etc., water, and the like.

Temperatures for the reaction are usually at approximately 4° C. to 40° C. and preferably approximately 4° C. to 25° C.

In the reaction solution, pH is usually approximately 5 to 10, preferably approximately 6 to 9, more preferably approximately 7 to 8 and most preferably approximately 7.5.

As described above, coelenterazine analogues are preferred as the luciferin, with particular preference being bis-coelenterazine.

The luciferin may also be added to the reaction system in the form of a solution in a polar solvent such as dimethylformamide, dimethylsulfoxide, etc., or in an alcohol such as methanol, ethanol, butanol, etc.

Activation of Luminescence Activity

The luminescence activity of the protein of the invention where luciferin serves as a substrate is activated by halide ions, nonionic surfactants, etc.

Examples of the halide ions are fluorine ions, chlorine ions, bromine ions and iodine ions; preferred are chlorine ions, bromine ions and iodine ions.

The concentration of the halide ions is usually approximately 10 µM to 100 mM, preferably approximately 100 µM to 50 mM and particularly preferably approximately 1 mM to 20 mM.

To add the halide ions to the reaction system, there is a method which comprises adding them in a salt form. The salts used are alkali metal salts such as sodium salts, potassium salts, etc.; alkaline earth metal salts such as calcium salts, magnesium salts, barium salts, etc. More specific examples are NaF, NaCl, NaBr, NaI KF, KCl, KBr, KI, $CaF_2$, $CaCl_2$, $CaBr_2$, $CaI_2$, $MgF_2$, $MgCl_2$, $MgBr_2$, $MgI_2$, etc.

Examples of nonionic surfactants which are commercially available (trade name) include Tween 20 (polyoxyethylene sorbitan monolaurate), Tween 80 (polyoxyethylene sorbitan monooleate), Triton X-100 (polyethylene glycol-p-isooctylphenyl ether), Briji-58 (polyoxyethylene (20) cetyl ether), Nonidet P-40 (ethylphenolpoly(ethylene glycol ether)n), and the like, and preferably, Tween 20, Triton X-100, etc.

Concentration of the nonionic surfactant is generally about 0.0002% (w/v) to about 0.2% (w/v), preferably, about 0.001% (w/v) to about 0.1% (w/v), and particularly preferably, about 0.05% (w/v) to about 0.02% (w/v).

Regardless of their purposes, all of the documents and publications described in the specification are incorporated herein by reference, each in its respective entirety.

Unless otherwise indicated with respect to the embodiments and working examples, the methods described in standard sets of protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., etc., or modifications or variations thereof are used. When commercially available reagent kits or measuring apparatuses are used, protocols attached to them are used unless otherwise indicated.

The objects, characteristics and advantages of the present invention as well as the idea thereof are apparent to those skilled in the art from the descriptions given herein. Based on the description given herein, those skilled in the art can easily work the present invention.

It can be understood that the best mode for carrying out the invention, specific working examples, etc. are disclosed as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLES

Hereinafter, the present invention will be described with reference to EXAMPLES below but is not deemed to limit the invention thereto.

Example 1

Design and Chemical Synthesis of Codon-optimized Nucleic Acid

Based on the amino acid sequence (SEQ ID NO: 1) of the catalytic 19 kDa domain (sometimes simply referred to as nanoLuc) in the mutant *Oplophorus* luciferase from Promega Corp. generated by mutagenesis of the catalytic 19 kDa domain (sometimes simply referred to as nanoKAZ) of native *Oplophorus* luciferase, a gene for the mutated catalytic 19 kDa domain (sometimes simply referred to as nanoKAZ) of the codon-optimized *Oplophorus* luciferase was designed. Specifically, the nucleotide sequence (SEQ ID NO: 2) of nanoKAZ was designed by applying only the amino acid codon frequently used in human without changing the amino acid sequence (SEQ ID NO: 1) of nanoLuc. The codon usage frequency of the nanoKAZ domain is shown in TABLE 1. Obviously, the codon-optimized nanoKAZ domain nucleic acid was designed by adopting only the amino acid codon frequently used in human. The gene optimally designed for the codon-optimized nanoKAZ domain was chemically synthesized in a conventional manner.

TABLE 1

| 1st Base | 2nd Base U | | | 2nd Base C | | | 2nd Base A | | | 2nd Base G | | | 3rd Base |
|---|---|---|---|---|---|---|---|---|---|---|---|---|---|
| U | TTT | Phe | 0 | TCT | Ser | 0 | TAT | Tyr | 0 | TGT | Cys | 0 | T |
|   | TTC |     | 8 | TCC |     | 0 | TAC |     | 6 | TGC |     | 1 | C |
|   | TTA | Leu | 0 | TCA |     | 0 | TAA | end | 1 | TGA | end | 0 | A |
|   | TTG |     | 0 | TCG |     | 0 | TAG |     | 0 | TGG | Trp | 3 | G |
| C | CTT |     | 0 | CCT | Pro | 0 | CAT | His | 0 | CGT | Arg | 0 | T |
|   | CTC |     | 0 | CCC |     | 6 | CAC |     | 4 | CGC |     | 0 | C |
|   | CTA |     | 0 | CCA |     | 0 | CAA | Gln | 0 | CGA |     | 0 | A |
|   | CTG |     | 16| CCG |     | 0 | CAG |     | 0 | CGG |     | 0 | G |
| A | ATT | Ile | 0 | ACT | Thr | 0 | AAT | Asn | 0 | AGT | Ser | 0 | T |
|   | ATC |     | 18| ACC |     | 10| AAC |     | 8 | AGC |     | 6 | C |
|   | ATA |     | 0 | ACA |     | 0 | AAA | Lys | 0 | AGA | Arg | 7 | A |
|   | ATG | Met | 3 | ACG |     | 0 | AAG |     | 7 | AGG |     | 0 | G |
| G | GTT | Val | 0 | GCT | Ala | 0 | GAT | Asp | 0 | GGT | Gly | 0 | T |
|   | GTC |     | 18| GCC |     | 3 | GAC |     | 12| GGC |     | 20| C |
|   | GTA |     | 0 | GCA |     | 0 | GAA | Glu | 0 | GGA |     | 0 | A |
|   | GTG |     | 0 | GCG |     | 0 | GAG |     | 8 | GGG |     | 0 | G |

The idendity at the amino acid sequence level of nanoKAZ and nanoLuc to native KAZ of 169 amino acids is summarized in TABLE 2.

TABLE 2

|       | KAZ  | nanoKAZ          | nanoLuc          |
|-------|------|------------------|------------------|
| KAZ   | 100% | 90.5%<br>(16/169)| 90.5%<br>(16/169)|

The identity at the gene sequence level of nanoKAZ and nanoLuc to native KAZ is summarized in TABLE 3.

TABLE 3

|         | KAZ  | nanoKAZ | nanoLuc |
|---------|------|---------|---------|
| KAZ     | 100% | 72%     | 73%     |
| nanoKAZ | —    | 100%    | 82%     |
| nanoLuc | —    | —       | 100%    |

Example 2

Construction of Vector for Secretion and Expression of Codon-optimized nanoKAZ Domain Protein in Cultured Animal Cells (1) Expression Vector for Secretory Expression of Codon-Optimized nanoKAZ Domain Protein without a Signal Peptide Sequence for Secretion The gene fragment for the codon-optimized nanoKAZ domain containing a Kozak sequence was digested with the restriction enzymes of Asp817 and XbaI, and inserted into the Asp817-XbaI site of pcDNA3 vector (manufactured by Invitrogen Inc.) to construct pcDNA3-nanoKAZ vector (FIG. 1).

The nucleotide sequence of nanoKAZ encoded in the expression vector pcDNA3-nanoKAZ is shown in SEQ ID NO: 2 and its amino acid sequence in SEQ ID NO: 1.

Figure 2:
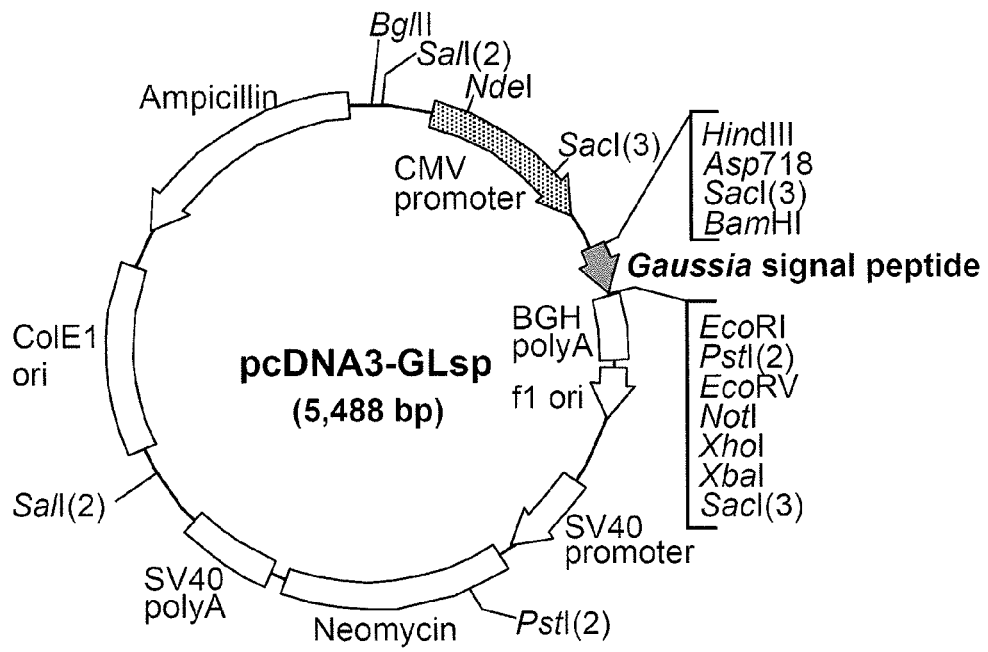
FIG. 2 shows the plasmid map of the expression vector pcDNA3-GLsp having a sequence for secretion of *Gaussia* luciferase.

(2) Expression Vector for Secretory Expression of the Codon-Optimized nanoKAZ Domain Protein with a Signal Peptide Sequence for Secretion of *Gaussia* Luciferase The vector for expressing the codon-optimized nanoKAZ domain protein was constructed as follows. Firstly, a novel expression vector pcDNA3-GLsp in cultured animal cells was constructed. Specifically, the signal pepetide sequence for secretion of *Gaussia* luciferase was obtained from pcDNA3-GLuc vector (manufactured by Prolume Ltd.) by PCR using primer GLsp-1R/EcoRI (SEQ ID NO: 3: 5' ggc GAATTC GGT GGG CTT GGC CTC GGC CAC 3', the EcoRI sequence underlined) and T7 primer (SEQ ID NO: 4: 5' TAATACG ACTCACTATAGGG 3'). After digesting with HindIII/EcoRI, the resulting fragment was inserted into the HindIII/EcoRI site, which are the restriction enzyme sites of pcDNA3 vector (manufactured by Invitrogen Inc.), to construct the novel expression vector pcDNA3-GLsp (FIG. 2). Namely, pcDNA3-GLsp is controlled by the CMV promoter, following by the Kozak sequence, the signal pepetide sequence for secretion of *Gaussia* luciferase and the multiple cloning sites.

Figure 3:
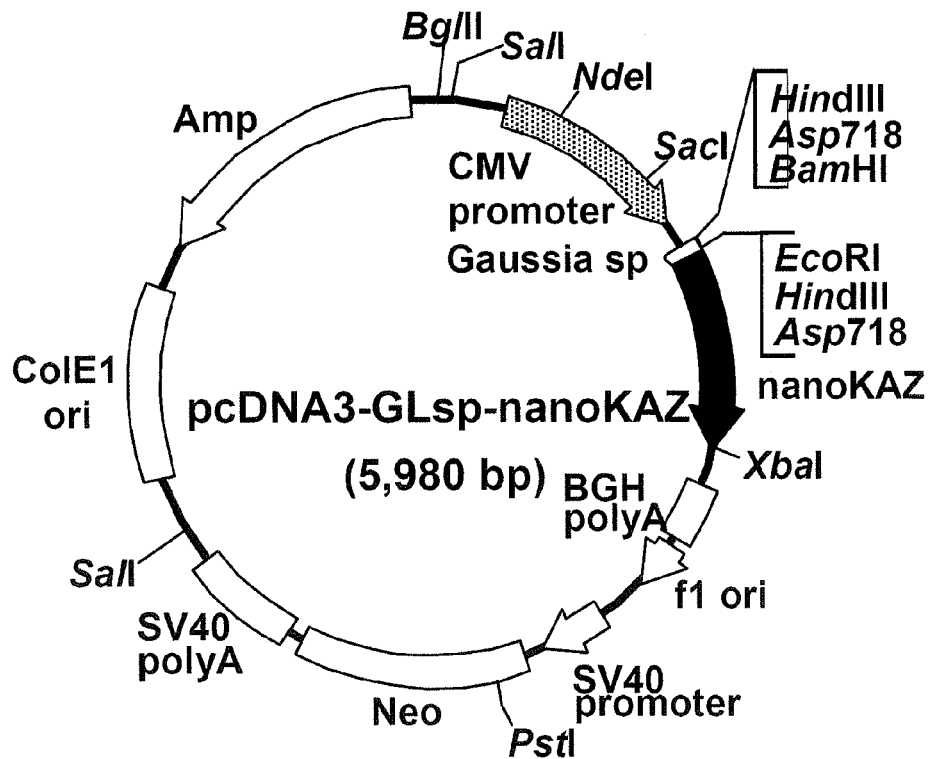
FIG. 3 shows the plasmid map of the vector pcDNA3-GLsp-nanoKAZ which expresses and secretes the codon-optimized nanoKAZ domain protein using a secretory signal of *Gaussia* luciferase.

Next, the codon-optimized nanoKAZ domain protein expression vector pcDNA3-GLsp-nanoKAZ (FIG. 3) was constructed using the novel expression vector pcDNA3-GLsp as follows. The gene fragment of the codon-optimized nanoKAZ domain was digested with restriction enzymes EcoRI/XbaI in a conventional manner, followed by ligation to the EcoRI-XbaI site of pcDNA3-GLsp to construct the expression vector pcDNA3-GLsp-nanoKAZ as shown in FIG. 3. The inserted gene sequence was confirmed by nucleotide sequencing with a DNA sequencer (manufactured by ABI Co.)

The nucleotide sequence of GLsp-nanoKAZ encoded in the expression vector pcDNA3-GLsp-nanoKAZ is shown in SEQ ID NO: 5 and the amino acid sequence in SEQ ID NO: 6. The amino acid sequence of secreted protein is shown in SEQ ID NO: 7.

Example 3

Transfection of Vector into Cultured Animal Cells and Preparation of Enzyme for Assay
(1) Purification of Expression Plasmid Using the plasmids pcDNA3-nanoKAZ and pcDNA3-GLsp-nanoKAZ obtained in EXAMPLE 2, the following experiment was carried out. The plasmids pcDNA3-nanoKAZ and pcDNA3-GLsp-nanoKAZ were purified from *Escherichia coli* JM83 using a Plasmid Purification Kit (manufactured by QIAGEN Inc.) and dissolved in sterile water to a concentration of 1 µg/µL. Following by the similar procedures, firefly luciferase vector (pGL4.13 [Luc2/sv40]: manufactured by Promega Corp.) was used as an internal standard.
(2) Transfection and Preparation of Enzyme for Assay CHO—K1 cell line derived from Chinese hamster ovary was cultured in Ham's F-12 medium (manufactured by Wako Pure Chemical Industries, Ltd.). containing 10% (v/v) fetal bovine serum (manufactured by Biowest Inc.), and HeLa cell line derived from human uterine cervical cancer cells and COS-1 cell line derived from African green monkey kidney were cultured in DMEME (manufactured by Wako Pure Chemical Industries, Ltd.) containing 10% (v/v) fetal bovine serum (manufactured by Biowest Inc.). The respective cells were plated onto 6 well plates in $1\times10^5$ cells/well/2 mL medium (n=2) and cultured in incubators at 37° C. in 5% (v/v) $CO_2$. Twenty-four hours later, the purified pcDNA3-nanoKAZ or pcDNA3-GLsp-nanoKAZ plasmid was transfected into CHO cells using a FuGene HD (manufactured by Promega Corp.) transfection kit, which was used in the following experiment. Specifically, 1 µg of pcDNA3-nanoKAZ expression vector or 1 µg of pcDNA3-GLsp-nanoKAZ expression vector with 0.1 µg of pGL4.13 [Luc2/sv40] internal standard vector and 3 µL of FuGene HD were added to 100 µL of the medium, which was allowed to stand for 15 minutes at room temperature. A DNA-FuGene complex solution of 100 µL was added to cells in 6 wells. After incubation for 48 hours, the culture medium was recovered and used as a solution for assaying secretory nanoKAZ enzyme. On the other hand, nanoKAZ expressed in the cells were washed 3 times with 3 mL of 1× PBS, suspended in 1 mL of 1× PBS and sonicated on ice. The resultant cell extracts were used as an enzyme solution of nanoKAZ.

Example 4

Assay for Luminescence Activity of Codon-optimized nanoKAZ Domain Protein Expressed in Cultured Animal Cells
Determination of Luminescent Activity in Cultured Animal Cells The luminescence reaction was started by addition of 5 µL of the enzyme solution for assay obtained in EXAMPLE 3 to 100 µL of 50 mM Tris-HCl (pH 7.6)-10 mM EDTA (Wako Pure Chemical Industries, Ltd.) containing 0.5 µg of coelenterazine (manufactured by JNC Corp.). The luminescence activity was measured for 60 seconds with a luminometer (manufactured by Atto Co.: AB2200). The maximum intensity of luminescence ($I_{max}$) and the luminescence activity integrated for 60 seconds were represented as relative light units (rlu). On the other hand, the luminescence activity of firefly luciferase was used as an internal standard to confirm the efficiency of transfection. Five microliters of the enzyme solution for assay obtained in EXAMPLE 3 was added to 100 µL of the enzyme assay solution (manufactured by Promega Corp.) to start the luminescence reaction. The luminescence activity was measured with a luminometer (manufactured by Atto Co.: AB2200) by integration of luminescence for 10 seconds, which was shown as relative light units (rlu). As a result, the luminescence activity of firefly luciferase was found to be pcDNA3-nanoKAZ: 7,827 rlu and pcDNA3-GLsp-nanoKAZ: 6,865 rlu in CHO—K1 cells; pcDNA3-nanoKAZ: 1,970 rlu and pcDNA3-GLsp-nanoKAZ: 1,787 rlu in HeLa cells; and, pcDNA3-nanoKAZ: 28,232 rlu and pcDNA3-GLsp-nanoKAZ: 31,380 rlu in COS-1 cells. While the transfection efficiencies vary in depending upon cell types, the transfection efficiencies of pcDNA3-nanoKAZ and pcDNA3-GLsp-nanoKAZ are almost the same. The results obtained by measuring the luminescence activity of CHO—K1 cells, HeLa cells and COS-1 cells in culture medium and cells are shown in TABLE 4. Evidently, pcDNA3-nanoKAZ without a signal peptide sequence for secretion was secreted comparably or more efficiently than pcDNA3-GLsp-nanoKAZ. Namely, it was revealed that the expression vector pcDNA3-nanoKAZ bearing the codon-optimized nanoKAZ domain gene can secret nanoKAZ without a signal peptide sequence for secretion.

TABLE 4

Comparison of Extracellular Secretory Activities in Codon-Optimized nanoKAZ Domain among Cell Types Using Coelenterazine as a Light-Emitting Substrate

| | Maximum luminescence intensity ($I_{max}$, rlu/250 cell counts) | | | | | |
|---|---|---|---|---|---|---|
| | CHO-K1 cells | | HeLa cels | | COS-1 cells | |
| Expression vector | Culture medium | Cell extracts | Culture medium | Cell extracts | Culture medium | Cell extracts |
| pcDNA3-nanoKAZ | 6,232 | 9,760 | 3,213 | 7,124 | 5,157 | 10,186 |
| pcDNA3-GLsp-nanoKAZ | 4,194 | 779 | 6,868 | 656 | 6,499 | 1,372 |
| Blank | 5 | 3 | 6 | 3 | 6 | 3 |

Example 5

Figure 4:
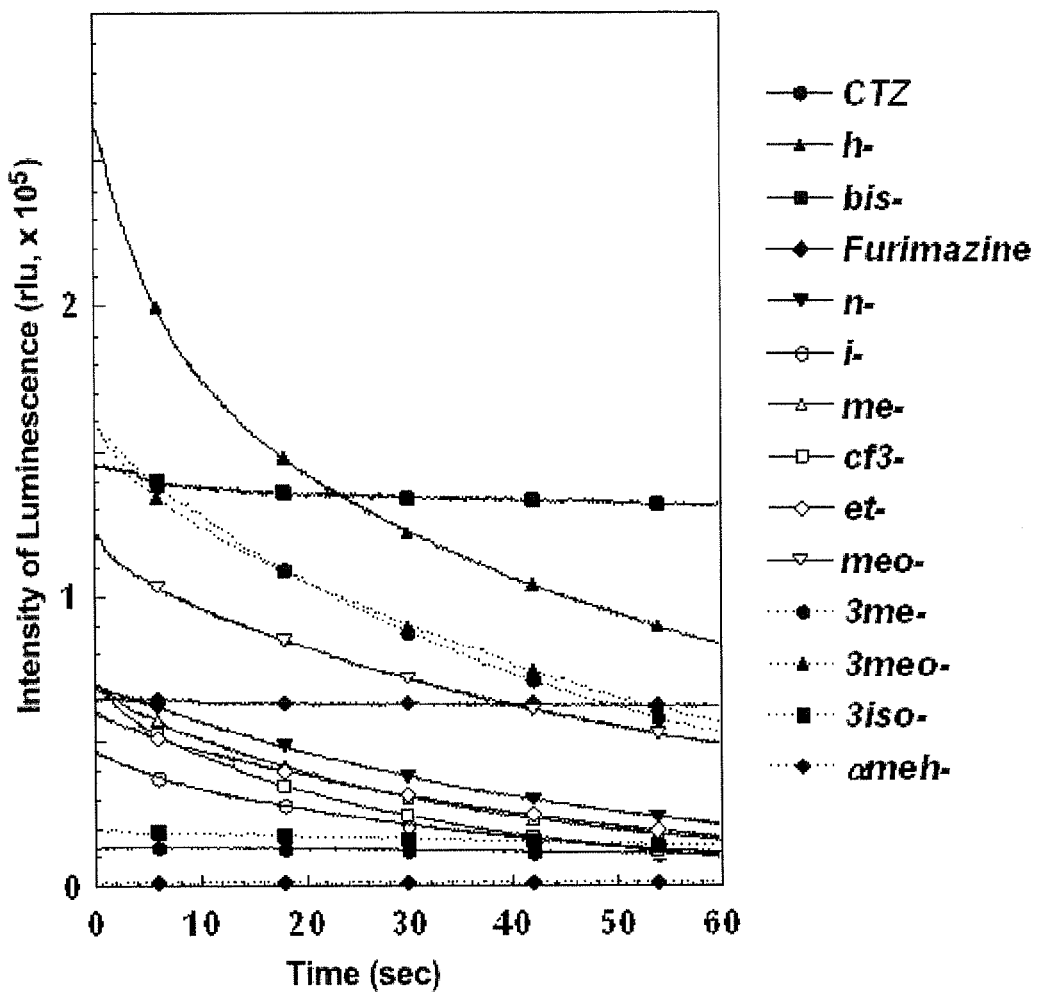
FIG. 4 shows comparison of recombinant nanoKAZ in substrate specificities and luminescence patterns.

Comparison of Codon-optimized nanoKAZ Domain in Substrate Specificities and Luminescence Patterns Coelenterazine analogues used in the substrate specificity experiments were synthesized by the methods described in the respective papers. More specifically, bis-coelenterazine, furimazine and C2-coelenterazine analogue were synthesized by the methods described in Nakamura et al. (1997) Tetrahedron Lett. 38:6405-6406, Hall et al. (2012) ACS Chem. Biol. 16; 848-1857 and Inouye et al. (2010) Anal. Biochem. 407: 247-252, respectively. Using as an enzyme solution for coelenterazine or its analogues the culture medium, into which nanoKAZ was secreted as described in EXAMPLE 4, the luminescence activity was measured. As a result, the substrate specificity for nanoKAZ was shown in TABLE 5. Among coelenterazine analogues, the relative maximum intensity of luminescence for h-, bis-, 3me- and 3meo-coelenterazines was at least 10-fold higher and the relative luminescence activity integrated for 1 minute of h- and bis-coelenterazines was at least 10-fold higher, than the others. These luminescence patterns are illustrated in FIG. 4. As shown in FIG. 4, bis-coelenterazine, furimazine and 3 iso-coelenterazine did not show the rapid-decay luminescence patterns. Consequently, the luminescence intensity and integrated luminescence level of these analogues exhibited at least 10-fold higher than that of coelenterazine. The light-emitting substrate which enabled the combination for continuous emission without decay of luminescence was found to be bis-coelenterazine. It was revealed that bis-coelenterazine displayed the activity of at least 2-fold higher than that of furimazine reported before, indicating that the light-emitting function was markedly improved.

TABLE 5

Substrate Specificity of the Codon-Optimized nanoKAZ Domain Protein

| Coelenterazine analogue | Relative maximum luminescence intensity ($I_{max}$) | Relative luminescence activity integrated (1 min) |
|---|---|---|
| Coelenterazine (CTZ) | 1.0 | 1.0 |
| h-Coelenterazine | 17.1 | 11.1 |
| bis-Coelenterazine | 10.8 | 11.5 |
| Furimazine | 4.8 | 5.3 |
| n-Coelenterazine | 4.9 | 3.3 |
| i-Coelenterazine | 3.3 | 2.0 |
| me-Coelenterazine | 5.2 | 3.0 |
| cf3-Coelenterazine | 5.2 | 2.4 |
| et-Coelenterazine | 4.4 | 2.8 |
| meo-Coelenterazine | 8.9 | 6.3 |
| 3me-Coelenterazine | 11.5 | 7.9 |
| 3meo-Coelenterazine | 11.6 | 8.2 |
| 3iso-Coelenterazine | 1.5 | 1.4 |
| ameh-Coelenterazine | 0.1 | 0.1 |

Example 6

Construction of Expression Vector to Express Codon-optimized nanoKAZ in *Escherichia coli*

Figure 5:
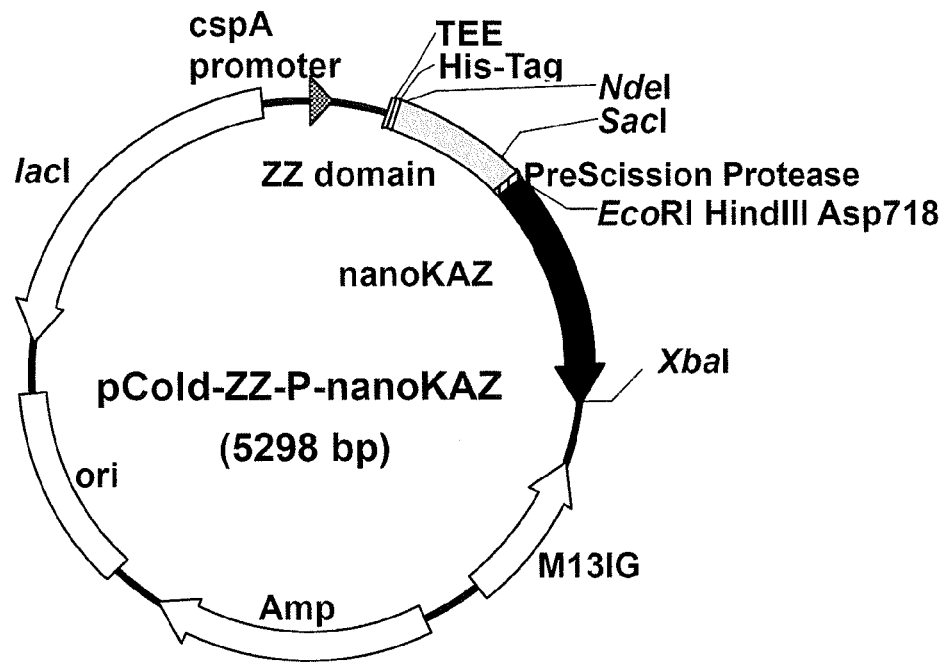
FIG. 5 shows the plasmid map of the vector pCold-ZZ-P-nanoKAZ which expresses the fusion protein of the codon-optimized nanoKAZ domain protein and the ZZ domain in *Escherichia coli*.

Expression vector pCold-ZZ-X (described in Inouye & Sahara, Protein Express. Purif. (2009) 66:52-57) was used to express the codon-optimized nanoKAZ in *Escherichia coli* as a host. The gene encoding the codon-optimized nanoKAZ domain was cloned into the EcoRI/XbaI site of this expression vector to construct the pCold-ZZ-P-nanoKAZ plasmid capable of expressing the nanoKAZ protein fused to the ZZ domain (FIG. 5). The nucleotide sequence of the gene encoding the codon-optimized nanoKAZ domain was confirmed by a DNA sequencer (manufactured by ABI).

Example 7

Expression and Purification of Codon-optimized nanoKAZ Domain in *Escherichia coli*

The recombinant nanoKAZ domain was purified in accordance with the following procedures. Firstly, the fusion protein was expressed in *Escherichia coli* cells as a soluble protein. The protein expressed had the histidine tag containing 6 histidine residues, ZZ domain, protease cleavage site and target protein (i.e., recombinant nanoKAZ domain). Next, as a first trial, the soluble fraction containing the fusion protein expressed in *Escherichia coli* cells was applied to a nickel chelate column. Then, the fraction adsorbed onto the column was collected as the fraction containing the fusion protein. Further, the fusion protein was eluted from the column followed by cleavage with protease. Furthermore, the cleaved fragment of the fusion protein was applied to a nickel chelate column as a second trial, and the fraction which was flown through the column was recovered. The flow-through fraction contained the target protein, recombinant nanoKAZ domain. The uncleaved fusion protein and the cleaved histidine tagged ZZ domain were adsorbed onto the gel. These procedures are described below in detail.

(i) Expression and Purification of his-ZZ-P-nanoKAZ as a Soluble Protein

The recombinant plasmid pCold-ZZ-P-nanoKAZ prepared in EXAMPLE 6 was used to express the codon-optimized nanoKAZ domain protein (hereinafter sometimes referred to as "nanoKAZ") in *Escherichia coli*. *Escherichia coli* strain BL21 (Novagen, Madison, Wis.) was used as the host cell. The BL21 strain having pCold-ZZ-P-nanoKAZ was cultured in 10 mL of Luria-Bertani medium supplemented with ampicillin (50 μg/mL) at 37° C. for 18 hours. The seed culture was inoculated into 400 mL of LB broth in a 3 L flask, incubated for 3 hours and then cooled with chilled water for an hour. After adding IPTG to the medium at the final concentration of 0.2 mM, the cells were incubated at 15° C. for further 20 hours. *Escherichia coli* was harvested from 800 mL of the culture medium by centrifugation at 5,000 rpm for 5 minutes, and suspended in 80 mL of 50 mM Tris-HCl (pH 7.6). *Escherichia coli* was disrupted by sonication using a Branson Model 250 Sonifier (Danbury, Conn.) 3 times for 3 minutes while cooling. After centrifugation at 12,000 rpm for 10 minutes, 70 mL of the supernatant containing ZZ-P-nanoKAZ was applied to a nickel chelate column (column size: 2.5×6 cm, manufactured by GE Healthcare) equilibrated with 50 mM Tris-HCl (pH 7.6). After the column was washed with 250 mL of 50 mM Tris-HCl (pH 7.6), the adsorbed His-ZZ-P-nanoKAZ was eluted with 0.1 M imidazole. The yield of the fusion protein ZZ-P-nanoKAZ was 37.2 mg from 800 mL of the cultured cells, with over 95% purity on SDS-PAGE analysis.

The nucleotide sequence of His-ZZ-P-nanoKAZ encoded in the recombinant plasmid pCold-ZZ-P-nanoKAZ is shown in SEQ ID NO: 8, and the amino acid sequence in SEQ ID NO: 9.

(ii) Digestion of his-ZZ-P-nanoKAZ with PreScission Protease

The conditions for digestion were as follows. His-ZZ-P-nanoKAZ (2.7 mg) eluted from the nickel chelate column was digested with 3 μg of PreScission Protease (manufactured by GE Healthcare) at 4° C. for 18 hours in 1 mL of 50 mM Tris-HCl (pH 7.6) containing 150 mM NaCl, 1 mM EDTA and 1 mM DTT.

(iii) Purification of Recombinant nanoKAZ

Figure 6:
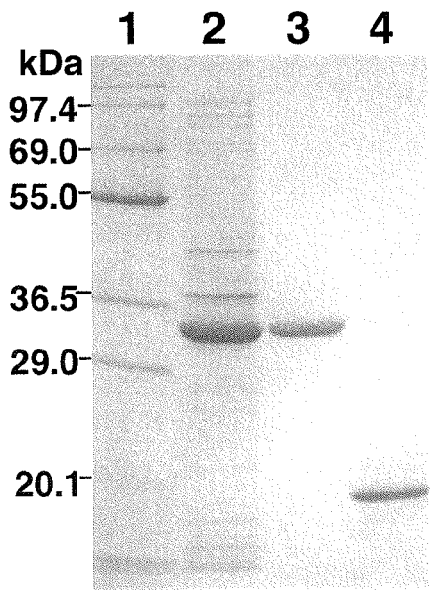
FIG. 6 shows SDS-PAGE analysis of recombinant nanoKAZ in the purification step. Lane 1: molecular weight marker, 2: crude extract, 3: nickel chelate gel-eluted ZZ-P-nanoKAZ fraction, 4: fraction not adsorbed onto nickel chelate containing nanoKAZ.

After digestion of His-ZZ-P-nanoKAZ with PreScission protease, the digested fraction contained the ZZ domain produced by the cleavage, recombinant nanoKAZ and uncleaved His-ZZ-P-nanoKAZ. To separate recombinant nanoKAZ from the cleaved ZZ domain and uncleaved His-ZZ-P-nanoKAZ, the PreScission protease treated solution was directly applied to 2 mL of a nickel chelate column (0.5×6 cm) equilibrated with 50 mM Tris-HCl (pH 7.6) and 0.7 mg of the recombinant nanoKAZ was recover from a flow-through fraction. The purified nanoKAZ protein had over 95% purity on SDS-PAGE analysis (FIG. 6).

Herein, the nucleotide sequence of recombinant nanoKAZ is shown in SEQ ID NO: 10 and the amino acid sequence in SEQ ID NO: 11.

The yields purified during the purification processes (i) to (iii) are summarized in TABLE 6.

TABLE 6

Yield of Purified nanoKAZ

| Step of purification | Total volume (mL) | Total protein (mg) (%) | Total activity (×10$^8$ rlu) (%) | Specific activity (×10$^8$/mg) |
|---|---|---|---|---|
| Crude extracts | 70 | 151 (100) | 420 (100) | 2.8 |
| Nickel chelate gel | 20 | 37 (25) | 196 (46) | 5.3 |
| PreScission cleavage | 1.5 | 2.7 (100) | 13.8 (100) | 5.1 |
| Nickel chelate gel | 1.0 | 0.7 (26) | 8.4 (61) | 12.0 |

Example 8

Assay for Luminescence Activity in the Purified Codon-optimized nanoKAZ Domain Protein The luminescence reaction was started by addition of 5 µl (0.03 µg) of the purified enzyme solution obtained in EXAMPLE 7 to 100 µl of 50 mM Tris-HCl (pH 7.6)-10 mM EDTA (Wako Pure Chemical Industries, Ltd.) containing 1 µg of coelenterazine (manufactured by JNC) or its analogues. The luminescence activity was measured with a luminometer (manufactured by Atto Co.: AB2200) for 60 seconds. The maximum intensity of luminescence ($I_{max}$) and the level integrated for 60 seconds were represented as relative light units (rlu).

Example 9

Substrate Specificity of the Purified Codon-optimized nanoKAZ Domain Protein

The luminescence activity of the purified codon-optimized nanoKAZ domain was measured in accordance with the method described in EXAMPLE 8. The results of substrate specificity for the purified nanoKAZ thus obtained are shown in TABLE 7. Among the coelenterazine analogues, the compounds that showed the relative maximum luminescence intensity of at least 10-fold higher than that of coelenterazine were h-, bis-, 3me- and 3meo-coelenterazines; h- and bis-coelenterazines showed the relative luminescence level integrated for 60 seconds of at least 10-fold higher than that of coelenterazine. The results obtained using the purified codon-optimized nanoKAZ as the enzyme solution are in good agreement with the results found by using the culture cell solution as the enzyme solution.

TABLE 7

Substrate Specificity for Purified nanoKAZ

| Coelenterazine analogue | Maximum luminescence intensity ($I_{max}$) | Relative luminescence activity integrated (1 min) |
|---|---|---|
| Coelenterazine (CTZ) | 1.0 | 1.0 |
| h-Coelenterazine | 19.7 | 12.5 |
| bis-Coelenterazine | 13.5 | 10.1 |
| Furimazine | 6.8 | 5.5 |
| n-Coelenterazine | 4.1 | 1.2 |
| i-Coelenterazine | 2.9 | 0.8 |
| me-Coelenterazine | 4.2 | 1.3 |
| cf3-Coelenterazine | 4.7 | 1.4 |
| et-Coelenterazine | 2.4 | 0.5 |
| meo-Coelenterazine | 7.7 | 3.4 |
| 3me-Coelenterazine | 10.3 | 4.2 |
| 3meo-Coelenterazine | 11.1 | 6.6 |
| 3iso-Coelenterazine | 1.1 | 0.9 |
| ameh-Coelenterazine | 0.1 | 0.1 |

Example 10

Spectroscopic Analysis by Measurement of Emission Spectra

The luminescence reaction was started by addition of a solution of substrate coelenterazine (5 µg/5 µL) in ethanol to a solution of nanoKAZ (3 µg) in 30 mM Tris-HCl (pH 7.6) containing 500 µl of 10 mM EDTA. The luminescence spectra were measured in a quartz cell with an optical path length of 10 mm, with a fluorescence spectrophotometer (manufactured by JASCO Corp., FP-6500) with the excitation light source turned off to correct for the spectra. The measurement conditions used were as follows: band width: 20 nm, response: 0.5 second, scan speed: 2000 nm/min at 22-25° C. The maximum intensity of luminescence ($\lambda_{max}$, nm) and half bandwidth (nm) were determined from the luminescence spectra measured, which are summarized in TABLE 8. The results of the spectra reveal that the maximum luminescence wavelengths were observed between 425 nm and 462 nm and the half bandwidth between 71 nm and 75 nm, indicating that C2- and C6-coelenterazine analogues did not affect the luminescence spectra.

TABLE 8

Comparison of Luminescence Spectra by Purified nanoKAZ using Coelenterazine Analogues

| Coelenterazine analogue | Maximum wavelength $\lambda_{max}$ (nm) | Half bandwidth FWHM (nm) |
|---|---|---|
| Coelenterazine (CTZ) | 457 | 73 |
| h-Coelenterazine | 455 | 71 |
| bis-Coelenterazine | 453 | 73 |
| Furimazine | 452 | 73 |
| n-Coelenterazine | 454 | 71 |
| i-Coelenterazine | 457 | 73 |
| me-Coelenterazine | 460 | 75 |
| cf3-Coelenterazine | 454 | 71 |
| et-Coelenterazine | 458 | 75 |
| meo-Coelenterazine | 458 | 73 |
| 3me-Coelenterazine | 458 | 73 |
| 3meo-Coelenterazine | 458 | 71 |
| 3iso-Coelenterazine | 460 | 75 |
| ameh-Coelenterazine | 462 | 73 |

Example 11

Comparison of Expression in Cultured Cell System Between nanoKAZ Gene and nanoLuc Gene

In order to compare the gene expression efficiency between the nanoKAZ gene and the nanoLuc gene in the cultured cell system, an expression vector that was different only in the nanoKAZ gene sequence and the nanoLuc gene sequence was constructed. The expression vector constructed was transfected to CHO—K1 cells. Then, the expression level of luciferase activity was compared by the following procedure. In the nanoLuc gene, the gene sequence described in Hall et al. (2012) ACS Chem. Biol. 16; 848-1857 was chemically synthesized and provided for use.

(1) Construction of Vector to Assess Secretory Luciferase with Secretory Signal

Figure 7:
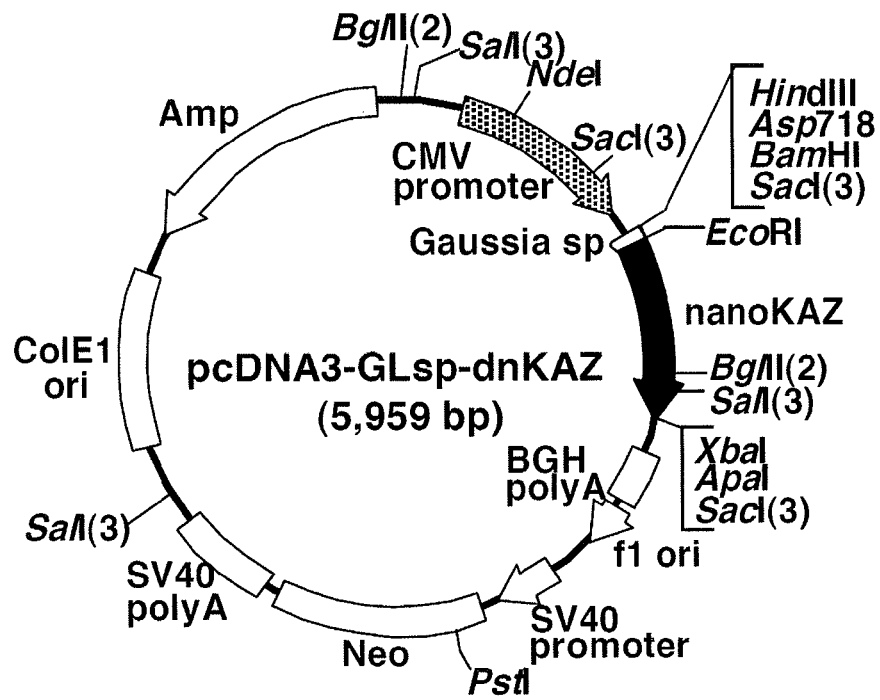
FIG. 7 shows the plasmid map of pcDNA3-GLsp-dnKAZ.
Figure 8:
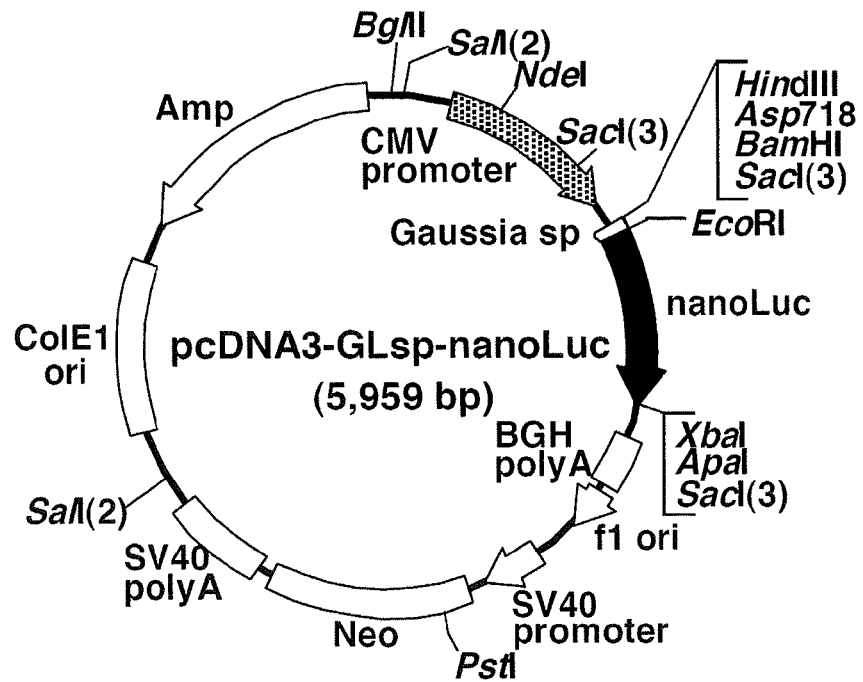
FIG. 8 shows the plasmid map of pcDNA3-GLsp-nanoLuc.

Expression vectors, pcDNA3-GLsp-dnKAZ (FIG. 7) and pcDNA3-GLsp-nanoLuc (FIG. 8), having the same promoter sequence, Kozak sequence and signal peptide sequence were constructed by the following procedures.

In pcDNA3-GLsp-dnKAZ, the sequence of 7 amino acids located at the amino terminus of nanoKAZ gene were removed to make the number of amino acids in nanoLuc identical, thus producing the ndKAZ gene fragment (dnKAZ fragment). Using pCold-ZZ-P-nanoKAZ as a template and using the primer nanoKAZ-1N/EcoRI (SEQ ID NO: 12: 5' gcgGAATTCTTCACCCTGGAGGACTTCGTCGGC 3': the EcoRI sequence underlined) and the primer nanoKAZ-3C/XbaI (SEQ ID NO: 13: 5' gcc TCTAGATTAGGCCAGGATTCTCTCGCACAGTCT 3': the XbaI sequence underlined), the gene was amplified by PCR. The resultant fragment was digested with restriction enzymes of EcoRI/XbaI and then ligated to the EcoRI-XbaI site of pcDNA3-GLsp vector described in EXAMPLE 2 to construct pcDNA3-GLsp-dnKAZ. The nucleotide sequence of GLsp-dnKAZ encoded by the expression vector pcDNA3-GLsp-dnKAZ is shown in SEQ ID NO: 14 and the amino acid sequence in SEQ ID NO: 15. In addition, the amino acid sequence of screated protein is shown in SEQ ID NO: 16.

In the pcDNA3-GLsp-nanoLuc vector, gene amplification was performed by PCR using the chemically synthesized nanoLuc gene as a template with the primer nLuc-1N/EcoRI (SEQ ID NO: 17: 5' gcg GAATTCTTCACACTCGAAGATTTCGTTGGG 3, the EcoRI sequence underlined) and the primer nLuc-2C/XbaI (SEQ ID NO: 18: 5 gcc TCTAGATTACGCCAGAATGCGTTCGCACAGCCG 3': the XbaI sequence underlined). The resulting fragment was digested with restriction enzymes of EcoRI/XbaI, and then ligated to the EcoRI-XbaI site of pcDNA-GLsp vector described in EXAMPLE 2 to construct pcDNA3-GLsp-nanoLuc. The nucleotide sequence of GLsp-nanoLuc encoded by the expression vector pcDNA3-GLsp-nanoLuc is shown in SEQ ID NO: 19 and the amino acid sequence in SEQ ID NO: 15. The amino acid sequence of screated protein is also shown in SEQ ID NO: 16.

(2) Construction of the Vector to Assess Secretory Luciferase without Secretory Signal Expression vector pcDNA3-nanoLuc having the same promoter sequence and Kozak sequence as those of pcDNA3-nanoKAZ described in EXAMPLE 2 was used. The pcDNA3-nanoLuc vector was constructed as follows.

Figure 9:
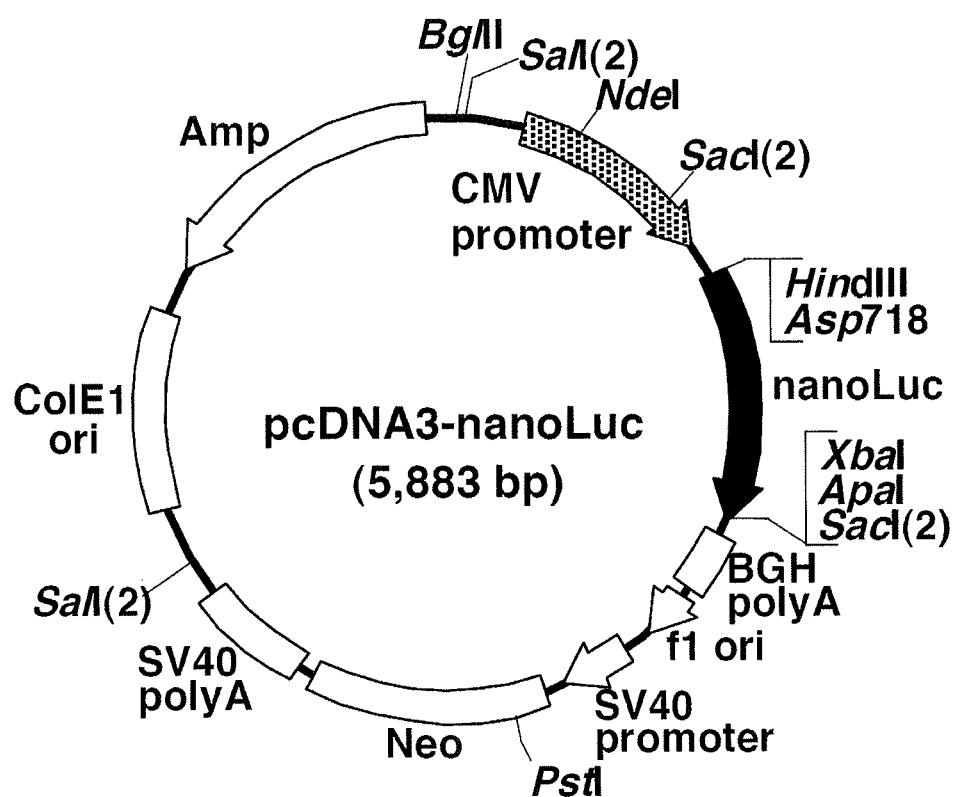
FIG. 9 shows the plasmid map of pcDNA3-nanoLuc.

Using the chemically synthesized nanoLuc as a template with the primer nLuc-3N/Asp718 (SEQ ID NO: 20: 5' gcg GGTACCACCATGGTCTTCACACTCGAAGATTTC 3': the underlined is the Asp718 sequence) and the primer nLuc-2C/XbaI (SEQ ID NO: 13), gene amplification was performed by PCR. The resulting fragment was digested with restriction enzymes Asp718/XbaI and then ligated to the Asp817-XbaI site of pcDNA3 vector (manufactured by Invitrogen Inc.) to construct the pcDNA3-nanoLuc (FIG. 9) vector. The nucleotide sequence of nanoLuc encoded by the expression vector pcDNA3-nanoLuc is shown in SEQ ID NO: 21 and the amino acid sequence in SEQ ID NO: 22.

(3) Comparison Between the nanoKAZ Gene and the nanoLuc Gene in Expression:

The vector was introduced into CHO—K1 cells by the method described in Example 3. After incubation for 23 hours, the culture medium and the cell extract were recovered. The luminescence activity in the culture medium and the cells was measured by the method described in EXAMPLE 4, using coelenterazine as a light-emitting substrate.

The results of the luminescence activity measured in the culture medium and the cells from CHO—K1 cells are shown in TABLE 9. It was confirmed from the results that the nanoKAZ gene without secretory signal was expressed about 2-fold higher in the culture medium and the cells, when the nanoLuc gene was used. With signal peptide, the nanoKAZ secreted into the culture medium showed the luminescence activity of about 1.4-fold higher than that of nanoLuc. It was thus revealed that the KAZ gene in accordance with the method for codon optimization of the present invention is superior to the nanoLuc gene, as a reporter gene for intracellular and extracellular expression.

TABLE 9

Comparison of Expression between nanoKAZ and nanoLuc Genes in CHO-K1 cells

| Expression vector | Maximum luminescence intensity ($I_{max}$, rlu/250 cells) | |
|---|---|---|
| | Culture medium | Cell extracts |
| 1) Without secretory signal peptide sequence | | |
| pcDNA3-nanoKAZ | 802 | 2689 |
| pcDNA3-nanoLuc | 432 | 1666 |
| 2) With secretory signal peptide sequence | | |
| pcDNA3-GLsp-dnKAZ | 1402 | 138 |
| pcDNA3-GLsp-nanoLuc | 1053 | 138 |
| 3) Blank | 5 | 3 |

[Sequence Listing Free Text]

[SEQ ID NO: 1] Amino acid sequence of nanoKAZ

[SEQ ID NO: 2] Nucleotide sequence of the polynucleotide encoding nanoKAZ

[SEQ ID NO: 3] Nucleotide sequence of the primer used in EXAMPLE 2

[SEQ ID NO: 4] Nucleotide sequence of the primer used in EXAMPLE 2

[SEQ ID NO: 5] Nucleotide sequence of the polynucleotide encoding GLsp-nanoKAZ

[SEQ ID NO: 6] Amino acid sequence of GLsp-nanoKAZ

[SEQ ID NO: 7] Amino acid sequence of GLsp-nanoKAZ after secretion

[SEQ ID NO: 8] Nucleotide sequence of the polynucleotide encoding His-ZZ-P-nanoKAZ

[SEQ ID NO: 9] Amino acid sequence of His-ZZ-P-nanoKAZ

[SEQ ID NO: 10] Nucleotide sequence of the polynucleotide encoding the recombinant nanoKAZ

[SEQ ID NO: 11] Amino acid sequence of the recombinant nanoKAZ
[SEQ ID NO: 12] Nucleotide sequence of the primer used in EXAMPLE 11
[SEQ ID NO: 13] Nucleotide sequence of the primer used in EXAMPLE 11
[SEQ ID NO: 14] Nucleotide sequence of the polynucleotide encoding GLsp-dnKAZ
[SEQ ID NO: 15] Amino acid sequences of GLsp-dnKAZ and GLsp-nanoLuc
[SEQ ID NO: 16] Amino acid sequences of GLsp-dnKAZ and GLsp-nanoLuc after secretion
[SEQ ID NO: 17] Nucleotide sequence of the primer used in EXAMPLE 11
[SEQ ID NO: 18] Nucleotide sequence of the primer used in EXAMPLE 11
[SEQ ID NO: 19] Nucleotide sequence of the polynucleotide encoding GLsp-nanoLuc
[SEQ ID NO: 20] Nucleotide sequence of the primer used in EXAMPLE 11
[SEQ ID NO: 21] Nucleotide sequence of the polynucleotide encoding nanoLuc
[SEQ ID NO: 22] Amino acid sequence of nanoLuc
[Sequence Listing]

The invention claimed is:

1. An isolated polynucleotide selected from the group consisting of (a) to (d) below:
   (a) a polynucleotide comprising a polynucleotide consisting of the nucleotide sequence of SEQ ID NO: 2;
   (b) polynucleotide comprising a polynucleotide encoding a protein consisting of a nucleotide sequence in which 1 to 20 nucleotides are deleted, substituted, inserted and/or added in the nucleotide sequence of SEQ ID NO: 2, and having a luminescent catalyst activity by using luciferin as a substrate;
   (c) a polynucleotide comprising a polynucleotide encoding a protein consisting of a nucleotide sequence having at least 90% identity to the nucleotide sequence of SEQ ID NO: 2, and having a luminescent catalyst activity by using lucifeuin as a substrate; and, (d) a polynucleotide comprising a polynucleotide encoding a protein which hybridizes to a polynucleotide consisting of a nucleotide sequence complementary to the nucleotide sequence of SEQ ID NO: 2 under high stringency conditions, and has a luminescent catalyst activity by using luciferin as a substrate, wherein the high stringency conditions are 5×SSC, 5×Denhardt's solution, 0.5% (w/v) SDS, 50% (v/v) formamide, and 50° C.

2. The polynucleotide according to claim 1, which is selected from the group consisting of (a) to (c) below:
    (a) a polynucleotide comprising a polynucleotide consisting of the nucleotide sequence of SEQ ID NO: 2;
    (b) a polynucleotide comprising a polynucleotide encoding a protein consisting of a nucleotide sequence in which 1 to 15 nucleotides are deleted, substituted, inserted and/or added in the nucleotide sequence of SEQ ID NO: 2, and having a luminescent catalyst activity by using luciferin as a substrate; and
    (c) a polynucleotide comprising a polynucleotide encoding a protein consisting of a nucleotide sequence having at least 95% identity to the nucleotide sequence of SEQ ID NO: 2, and having a luminescent catalyst activity by using luciferin as a substrate.

3. The polynucleotide according to claim 1, which is selected from the group consisting of (a) to (c) below:
    (a) a polynucleotide comprising a polynucleotide consisting of the nucleotide sequence of SEQ ID NO: 2;
    (b) a polynucleotide comprising a polynucleotide encoding a protein consisting of a nucleotide sequence in which 1 to 10 nucleotides are deleted, substituted, inserted and/or added in the nucleotide sequence of SEQ ID NO: 2, and having a luminescent catalyst activity by using luciferin as a substrate; and,
    (c) a polynucleotide comprising a polynucleotide encoding a protein consisting of a nucleotide sequence having at least 98% identity to the nucleotide sequence of SEQ ID NO: 2, and having a luminescent catalyst activity by using luciferin as a substrate.

4. An isolated polynucleotide comprising a polynucleotide consisting of the nucleotide sequence of SEQ ID NO: 2.

5. The polynucleotide according to claim 1, further comprising a polynucleotide encoding a polypeptide consisting of an amino acid sequence for promoting translation and/or a polynucleotide encoding a polypeptide consisting of an amino acid sequence for purification.

6. An isolated polynucleotide consisting of any one of the nucleotide sequences of SEQ ID NO: 5, SEQ ID NO: 8, SEQ ID NO: 10 and SEQ ID NO: 14.

7. A recombinant vector comprising the polynucleotide according to claim 1.

8. An isolated transformed host cell comprising the recombinant vector according to claim 7.

9. A method of producing a protein, which comprises the step of culturing the transformed host cell according to claim 8 to produce the protein encoded by the polynucleotide.

10. A kit comprising the polynucleotide according to claim 1, a recombinant vector comprising the polynucleotide or an isolated transformed host cell comprising the vector.

11. The kit according to claim 10, further comprising bis-coelenterazine.

* * * * *

```
                        SEQUENCE LISTING

<160> NUMBER OF SEQ ID NOS: 22

<210> SEQ ID NO 1
<211> LENGTH: 171
<212> TYPE: PRT
<213> ORGANISM: Artificial sequence
<220> FEATURE:
<223> OTHER INFORMATION: Synthetic Construct

<400> SEQUENCE: 1

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 2
<211> LENGTH: 516
<212> TYPE: DNA
<213> ORGANISM: Artificial sequence
<220> FEATURE:
<223> OTHER INFORMATION: synthetic DNA

<400> SEQUENCE: 2
atggtcttca ccctggagga cttcgtcggc gactggagac agaccgccgg ctacaacctg      60
gaccaggtcc tggagcaggg cggcgtcagc agcctgttcc agaacctggg cgtcagcgtc     120
acccccatcc agagaatcgt ccttagcggc gagaacggcc tgaagatcga catccacgtc     180
atcatcccct acgagggcct gagcggcgac cagatgggcc agatcgagaa gatcttcaag     240
```

```
gtcgtctacc ccgtcgacga ccaccacttc aaggtcatcc tgcactacgg cacccctggtc    300 atcgacggcg tcaccccaa catgatcgac tacttcggta gaccctacga gggcatcgcc      360
gtcttcgacg gcaagaagat caccgtcacc ggcaccctgt ggaacggcaa caagatcatc     420
gacgagagac tgatcaaccc cgacggcagc ctgctgttca gagtcaccat caacggcgtc     480
accggctgga gactgtgcga gagaatcctg gcctaa                               516

<210> SEQ ID NO 3
<211> LENGTH: 30
<212> TYPE: DNA
<213> ORGANISM: Artificial sequence
<220> FEATURE:
<223> OTHER INFORMATION: synthetic DNA

<400> SEQUENCE: 3
ggcgaattcg gtgggcttgg cctcggccac                                      30

<210> SEQ ID NO 4
<211> LENGTH: 20
<212> TYPE: DNA
<213> ORGANISM: Artificial sequence
<220> FEATURE:
<223> OTHER INFORMATION: synthetic DNA

<400> SEQUENCE: 4
taatacgact cactataggg                                                 20

<210> SEQ ID NO 5
<211> LENGTH: 597
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(597)

<400> SEQUENCE: 5 atg gga gtc aaa gtt ctg ttt gcc ctg atc tgc atc gct gtg gcc gag     48
Met Gly Val Lys Val Leu Phe Ala Leu Ile Cys Ile Ala Val Ala Glu
1               5                   10                  15 gcc aag ccc acc gaa ttc aag ctt ggt acc acc atg gtc ttc acc ctg     96
Ala Lys Pro Thr Glu Phe Lys Leu Gly Thr Thr Met Val Phe Thr Leu
            20                  25                  30 gag gac ttc gtc ggc gac tgg aga cag acc gcc ggc tac aac ctg gac    144
Glu Asp Phe Val Gly Asp Trp Arg Gln Thr Ala Gly Tyr Asn Leu Asp
        35                  40                  45 cag gtc ctg gag cag ggc ggc gtc agc agc ctg ttc cag aac ctg ggc    192
Gln Val Leu Glu Gln Gly Gly Val Ser Ser Leu Phe Gln Asn Leu Gly
    50                  55                  60 gtc agc gtc acc ccc atc cag aga atc gtc ctt agc ggc gag aac ggc    240
Val Ser Val Thr Pro Ile Gln Arg Ile Val Leu Ser Gly Glu Asn Gly
65                  70                  75                  80 ctg aag atc gac atc cac gtc atc atc ccc tac gag ggc ctg agc ggc    288
Leu Lys Ile Asp Ile His Val Ile Ile Pro Tyr Glu Gly Leu Ser Gly
                85                  90                  95 gac cag atg ggc cag atc gag aag atc ttc aag gtc gtc tac ccc gtc    336
Asp Gln Met Gly Gln Ile Glu Lys Ile Phe Lys Val Val Tyr Pro Val
            100                 105                 110 gac gac cac cac ttc aag gtc atc ctg cac tac ggc acc ctg gtc atc    384
Asp Asp His His Phe Lys Val Ile Leu His Tyr Gly Thr Leu Val Ile
        115                 120                 125
```

```
gac ggc gtc acc ccc aac atg atc gac tac ttc ggt aga ccc tac gag    432
Asp Gly Val Thr Pro Asn Met Ile Asp Tyr Phe Gly Arg Pro Tyr Glu
        130                 135                 140 ggc atc gcc gtc ttc gac ggc aag aag atc acc gtc acc ggc acc ctg    480
Gly Ile Ala Val Phe Asp Gly Lys Lys Ile Thr Val Thr Gly Thr Leu
145                 150                 155                 160 tgg aac ggc aac aag atc atc gac gag aga ctg atc aac ccc gac ggc    528
Trp Asn Gly Asn Lys Ile Ile Asp Glu Arg Leu Ile Asn Pro Asp Gly
                165                 170                 175 agc ctg ctg ttc aga gtc acc atc aac ggc gtc acc ggc tgg aga ctg    576
Ser Leu Leu Phe Arg Val Thr Ile Asn Gly Val Thr Gly Trp Arg Leu
            180                 185                 190 tgc gag aga atc ctg gcc taa                                        597
Cys Glu Arg Ile Leu Ala
            195
```

<210> SEQ ID NO 6
<211> LENGTH: 198
<212> TYPE: PRT
<213> ORGANISM: Artificial sequence
<220> FEATURE:
<223> OTHER INFORMATION: Synthetic Construct

<400> SEQUENCE: 6

```
Met Gly Val Lys Val Leu Phe Ala Leu Ile Cys Ile Ala Val Ala Glu
1               5                   10                  15

Ala Lys Pro Thr Glu Phe Lys Leu Gly Thr Thr Met Val Phe Thr Leu
            20                  25                  30

Glu Asp Phe Val Gly Asp Trp Arg Gln Thr Ala Gly Tyr Asn Leu Asp
        35                  40                  45

Gln Val Leu Glu Gln Gly Gly Val Ser Ser Leu Phe Gln Asn Leu Gly
    50                  55                  60

Val Ser Val Thr Pro Ile Gln Arg Ile Val Leu Ser Gly Glu Asn Gly
65                  70                  75                  80

Leu Lys Ile Asp Ile His Val Ile Ile Pro Tyr Glu Gly Leu Ser Gly
                85                  90                  95

Asp Gln Met Gly Gln Ile Glu Lys Ile Phe Lys Val Val Tyr Pro Val
            100                 105                 110

Asp Asp His His Phe Lys Val Ile Leu His Tyr Gly Thr Leu Val Ile
        115                 120                 125

Asp Gly Val Thr Pro Asn Met Ile Asp Tyr Phe Gly Arg Pro Tyr Glu
    130                 135                 140

Gly Ile Ala Val Phe Asp Gly Lys Lys Ile Thr Val Thr Gly Thr Leu
145                 150                 155                 160

Trp Asn Gly Asn Lys Ile Ile Asp Glu Arg Leu Ile Asn Pro Asp Gly
                165                 170                 175

Ser Leu Leu Phe Arg Val Thr Ile Asn Gly Val Thr Gly Trp Arg Leu
            180                 185                 190

Cys Glu Arg Ile Leu Ala
            195
```

<210> SEQ ID NO 7
<211> LENGTH: 181
<212> TYPE: PRT
<213> ORGANISM: Artificial sequence
<220> FEATURE:
<223> OTHER INFORMATION: Synthetic Construct

<400> SEQUENCE: 7

```
Lys Pro Thr Glu Phe Lys Leu Gly Thr Thr Met Val Phe Thr Leu Glu
1               5                   10                  15

Asp Phe Val Gly Asp Trp Arg Gln Thr Ala Gly Tyr Asn Leu Asp Gln
            20                  25                  30

Val Leu Glu Gln Gly Gly Val Ser Ser Leu Phe Gln Asn Leu Gly Val
        35                  40                  45

Ser Val Thr Pro Ile Gln Arg Ile Val Leu Ser Gly Glu Asn Gly Leu
    50                  55                  60

Lys Ile Asp Ile His Val Ile Ile Pro Tyr Glu Gly Leu Ser Gly Asp
65                  70                  75                  80

Gln Met Gly Gln Ile Glu Lys Ile Phe Lys Val Val Tyr Pro Val Asp
                85                  90                  95

Asp His His Phe Lys Val Ile Leu His Tyr Gly Thr Leu Val Ile Asp
            100                 105                 110

Gly Val Thr Pro Asn Met Ile Asp Tyr Phe Gly Arg Pro Tyr Glu Gly
        115                 120                 125

Ile Ala Val Phe Asp Gly Lys Lys Ile Thr Val Thr Gly Thr Leu Trp
    130                 135                 140

Asn Gly Asn Lys Ile Ile Asp Glu Arg Leu Ile Asn Pro Asp Gly Ser
145                 150                 155                 160

Leu Leu Phe Arg Val Thr Ile Asn Gly Val Thr Gly Trp Arg Leu Cys
                165                 170                 175

Glu Arg Ile Leu Ala
            180
```

```
<210> SEQ ID NO 8
<211> LENGTH: 990
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(990)

<400> SEQUENCE: 8
```

```
atg aat cac aaa gtg cat cat cat cat cat cat atg gcg caa cac gat      48
Met Asn His Lys Val His His His His His His Met Ala Gln His Asp
1               5                   10                  15 gaa gcc gta gac aac aaa ttc aac aaa gaa caa caa aac gcg ttc tat      96
Glu Ala Val Asp Asn Lys Phe Asn Lys Glu Gln Gln Asn Ala Phe Tyr
            20                  25                  30 gag atc tta cat tta cct aac tta aac gaa gaa caa cga aac gcc ttc     144
Glu Ile Leu His Leu Pro Asn Leu Asn Glu Glu Gln Arg Asn Ala Phe
        35                  40                  45 atc caa agt tta aaa gat gac cca agc caa agc gct aac ctt tta gca     192
Ile Gln Ser Leu Lys Asp Asp Pro Ser Gln Ser Ala Asn Leu Leu Ala
    50                  55                  60 gaa gct aaa aag cta aat gat gct cag gcg ccg aaa gta gac aac aaa     240
Glu Ala Lys Lys Leu Asn Asp Ala Gln Ala Pro Lys Val Asp Asn Lys
65                  70                  75                  80 ttc aac aaa gaa caa caa aac gcg ttc tat gag atc tta cat tta cct     288
Phe Asn Lys Glu Gln Gln Asn Ala Phe Tyr Glu Ile Leu His Leu Pro
                85                  90                  95 aac tta aac gaa gaa caa cga aac gcc ttc atc caa agt tta aaa gat     336
Asn Leu Asn Glu Glu Gln Arg Asn Ala Phe Ile Gln Ser Leu Lys Asp
            100                 105                 110 gac cca agc caa agc gct aac ctt tta gca gaa gct aaa aag cta aat     384
Asp Pro Ser Gln Ser Ala Asn Leu Leu Ala Glu Ala Lys Lys Leu Asn
```

```
                115                    120                    125
gat gct cag gcg ccg aaa gta gac gca aat tcg agc tcg gga tct ctg        432
Asp Ala Gln Ala Pro Lys Val Asp Ala Asn Ser Ser Ser Gly Ser Leu
        130                    135                    140 gaa gtt ctg ttc cag ggg ccc gaa ttc aag ctt ggt acc acc atg gtc        480
Glu Val Leu Phe Gln Gly Pro Glu Phe Lys Leu Gly Thr Thr Met Val
145                    150                    155                    160 ttc acc ctg gag gac ttc gtc ggc gac tgg aga cag acc gcc ggc tac        528
Phe Thr Leu Glu Asp Phe Val Gly Asp Trp Arg Gln Thr Ala Gly Tyr
                165                    170                    175 aac ctg gac cag gtc ctg gag cag ggc ggc gtc agc agc ctg ttc cag        576
Asn Leu Asp Gln Val Leu Glu Gln Gly Gly Val Ser Ser Leu Phe Gln
            180                    185                    190 aac ctg ggc gtc agc gtc acc ccc atc cag aga atc gtc ctt agc ggc        624
Asn Leu Gly Val Ser Val Thr Pro Ile Gln Arg Ile Val Leu Ser Gly
        195                    200                    205 gag aac ggc ctg aag atc gac atc cac gtc atc atc ccc tac gag ggc        672
Glu Asn Gly Leu Lys Ile Asp Ile His Val Ile Ile Pro Tyr Glu Gly
210                    215                    220 ctg agc ggc gac cag atg ggc cag atc gag aag atc ttc aag gtc gtc        720
Leu Ser Gly Asp Gln Met Gly Gln Ile Glu Lys Ile Phe Lys Val Val
225                    230                    235                    240 tac ccc gtc gac gac cac cac ttc aag gtc atc ctg cac tac ggc acc        768
Tyr Pro Val Asp Asp His His Phe Lys Val Ile Leu His Tyr Gly Thr
                245                    250                    255 ctg gtc atc gac ggc gtc acc ccc aac atg atc gac tac ttc ggt aga        816
Leu Val Ile Asp Gly Val Thr Pro Asn Met Ile Asp Tyr Phe Gly Arg
            260                    265                    270 ccc tac gag ggc atc gcc gtc ttc gac ggc aag aag atc acc gtc acc        864
Pro Tyr Glu Gly Ile Ala Val Phe Asp Gly Lys Lys Ile Thr Val Thr
        275                    280                    285 ggc acc ctg tgg aac ggc aac aag atc atc gac gag aga ctg atc aac        912
Gly Thr Leu Trp Asn Gly Asn Lys Ile Ile Asp Glu Arg Leu Ile Asn
290                    295                    300 ccc gac ggc agc ctg ctg ttc aga gtc acc atc aac ggc gtc acc ggc        960
Pro Asp Gly Ser Leu Leu Phe Arg Val Thr Ile Asn Gly Val Thr Gly
305                    310                    315                    320 tgg aga ctg tgc gag aga atc ctg gcc taa                                990
Trp Arg Leu Cys Glu Arg Ile Leu Ala
                325

<210> SEQ ID NO 9
<211> LENGTH: 329
<212> TYPE: PRT
<213> ORGANISM: Artificial sequence
<220> FEATURE:
<223> OTHER INFORMATION: Synthetic Construct

<400> SEQUENCE: 9

Met Asn His Lys Val His His His His His Met Ala Gln His Asp
1               5                   10                  15

Glu Ala Val Asp Asn Lys Phe Asn Lys Glu Gln Gln Asn Ala Phe Tyr
                20                  25                  30

Glu Ile Leu His Leu Pro Asn Leu Asn Glu Glu Gln Arg Asn Ala Phe
            35                  40                  45

Ile Gln Ser Leu Lys Asp Asp Pro Ser Gln Ser Ala Asn Leu Leu Ala
        50                  55                  60

Glu Ala Lys Lys Leu Asn Asp Ala Gln Ala Pro Lys Val Asp Asn Lys
65                  70                  75                  80
```

```
Phe Asn Lys Glu Gln Gln Asn Ala Phe Tyr Glu Ile Leu His Leu Pro
                85                  90                  95
Asn Leu Asn Glu Glu Gln Arg Asn Ala Phe Ile Gln Ser Leu Lys Asp
            100                 105                 110
Asp Pro Ser Gln Ser Ala Asn Leu Leu Ala Glu Ala Lys Lys Leu Asn
        115                 120                 125
Asp Ala Gln Ala Pro Lys Val Asp Ala Asn Ser Ser Gly Ser Leu
    130                 135                 140
Glu Val Leu Phe Gln Gly Pro Glu Phe Lys Leu Gly Thr Thr Met Val
145                 150                 155                 160
Phe Thr Leu Glu Asp Phe Val Gly Asp Trp Arg Gln Thr Ala Gly Tyr
                165                 170                 175
Asn Leu Asp Gln Val Leu Glu Gln Gly Gly Val Ser Ser Leu Phe Gln
            180                 185                 190
Asn Leu Gly Val Ser Val Thr Pro Ile Gln Arg Ile Val Leu Ser Gly
        195                 200                 205
Glu Asn Gly Leu Lys Ile Asp Ile His Val Ile Ile Pro Tyr Glu Gly
    210                 215                 220
Leu Ser Gly Asp Gln Met Gly Gln Ile Glu Lys Ile Phe Lys Val Val
225                 230                 235                 240
Tyr Pro Val Asp Asp His His Phe Lys Val Ile Leu His Tyr Gly Thr
                245                 250                 255
Leu Val Ile Asp Gly Val Thr Pro Asn Met Ile Asp Tyr Phe Gly Arg
            260                 265                 270
Pro Tyr Glu Gly Ile Ala Val Phe Asp Gly Lys Lys Ile Thr Val Thr
        275                 280                 285
Gly Thr Leu Trp Asn Gly Asn Lys Ile Ile Asp Glu Arg Leu Ile Asn
    290                 295                 300
Pro Asp Gly Ser Leu Leu Phe Arg Val Thr Ile Asn Gly Val Thr Gly
305                 310                 315                 320
Trp Arg Leu Cys Glu Arg Ile Leu Ala
                325

<210> SEQ ID NO 10
<211> LENGTH: 543
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(543)

<400> SEQUENCE: 10 ggg ccc gaa ttc aag ctt ggt acc acc atg gtc ttc acc ctg gag gac    48
Gly Pro Glu Phe Lys Leu Gly Thr Thr Met Val Phe Thr Leu Glu Asp
1               5                   10                  15 ttc gtc ggc gac tgg aga cag acc gcc ggc tac aac ctg gac cag gtc    96
Phe Val Gly Asp Trp Arg Gln Thr Ala Gly Tyr Asn Leu Asp Gln Val
                20                  25                  30 ctg gag cag ggc ggc gtc agc agc ctg ttc cag aac ctg ggc gtc agc   144
Leu Glu Gln Gly Gly Val Ser Ser Leu Phe Gln Asn Leu Gly Val Ser
            35                  40                  45 gtc acc ccc atc cag aga atc gtc ctt agc ggc gag aac ggc ctg aag   192
Val Thr Pro Ile Gln Arg Ile Val Leu Ser Gly Glu Asn Gly Leu Lys
        50                  55                  60 atc gac atc cac gtc atc atc ccc tac gag ggc ctg agc ggc gac cag   240
Ile Asp Ile His Val Ile Ile Pro Tyr Glu Gly Leu Ser Gly Asp Gln
```

```
atg ggc cag atc gag aag atc ttc aag gtc gtc tac ccc gtc gac gac    288
Met Gly Gln Ile Glu Lys Ile Phe Lys Val Val Tyr Pro Val Asp Asp
                85                  90                  95 cac cac ttc aag gtc atc ctg cac tac ggc acc ctg gtc atc gac ggc    336
His His Phe Lys Val Ile Leu His Tyr Gly Thr Leu Val Ile Asp Gly
            100                 105                 110 gtc acc ccc aac atg atc gac tac ttc ggt aga ccc tac gag ggc atc    384
Val Thr Pro Asn Met Ile Asp Tyr Phe Gly Arg Pro Tyr Glu Gly Ile
        115                 120                 125 gcc gtc ttc gac ggc aag aag atc acc gtc acc ggc acc ctg tgg aac    432
Ala Val Phe Asp Gly Lys Lys Ile Thr Val Thr Gly Thr Leu Trp Asn
    130                 135                 140 ggc aac aag atc atc gac gag aga ctg atc aac ccc gac ggc agc ctg    480
Gly Asn Lys Ile Ile Asp Glu Arg Leu Ile Asn Pro Asp Gly Ser Leu
145                 150                 155                 160 ctg ttc aga gtc acc atc aac ggc gtc acc ggc tgg aga ctg tgc gag    528
Leu Phe Arg Val Thr Ile Asn Gly Val Thr Gly Trp Arg Leu Cys Glu
                165                 170                 175 aga atc ctg gcc taa                                                 543
Arg Ile Leu Ala
        180
```

<210> SEQ ID NO 11
<211> LENGTH: 180
<212> TYPE: PRT
<213> ORGANISM: Artificial sequence
<220> FEATURE:
<223> OTHER INFORMATION: Synthetic Construct

<400> SEQUENCE: 11

```
Gly Pro Glu Phe Lys Leu Gly Thr Thr Met Val Phe Thr Leu Glu Asp
1               5                   10                  15

Phe Val Gly Asp Trp Arg Gln Thr Ala Gly Tyr Asn Leu Asp Gln Val
                20                  25                  30

Leu Glu Gln Gly Gly Val Ser Ser Leu Phe Gln Asn Leu Gly Val Ser
            35                  40                  45

Val Thr Pro Ile Gln Arg Ile Val Leu Ser Gly Glu Asn Gly Leu Lys
        50                  55                  60

Ile Asp Ile His Val Ile Pro Tyr Glu Gly Leu Ser Gly Asp Gln
65                  70                  75                  80

Met Gly Gln Ile Glu Lys Ile Phe Lys Val Val Tyr Pro Val Asp Asp
                85                  90                  95

His His Phe Lys Val Ile Leu His Tyr Gly Thr Leu Val Ile Asp Gly
            100                 105                 110

Val Thr Pro Asn Met Ile Asp Tyr Phe Gly Arg Pro Tyr Glu Gly Ile
        115                 120                 125

Ala Val Phe Asp Gly Lys Lys Ile Thr Val Thr Gly Thr Leu Trp Asn
    130                 135                 140

Gly Asn Lys Ile Ile Asp Glu Arg Leu Ile Asn Pro Asp Gly Ser Leu
145                 150                 155                 160

Leu Phe Arg Val Thr Ile Asn Gly Val Thr Gly Trp Arg Leu Cys Glu
                165                 170                 175

Arg Ile Leu Ala
        180
```

<210> SEQ ID NO 12
<211> LENGTH: 33

```
<212> TYPE: DNA
<213> ORGANISM: Artificial sequence
<220> FEATURE:
<223> OTHER INFORMATION: synthetic DNA

<400> SEQUENCE: 12
gcggaattct tcaccctgga ggacttcgtc ggc                                    33

<210> SEQ ID NO 13
<211> LENGTH: 36
<212> TYPE: DNA
<213> ORGANISM: Artificial sequence
<220> FEATURE:
<223> OTHER INFORMATION: synthetic DNA

<400> SEQUENCE: 13
gcctctagat taggccagga ttctctcgca cagtct                                 36

<210> SEQ ID NO 14
<211> LENGTH: 576
<212> TYPE: DNA
<213> ORGANISM: Artificial sequence
<220> FEATURE:
<223> OTHER INFORMATION: synthetic DNA

<400> SEQUENCE: 14
atgggagtca agttctgtt tgccctgatc tgcatcgctg tggccgaggc caagcccacc         60
gaattcttca ccctggagga cttcgtcggc gactggagac agaccgccgg ctacaacctg       120
gaccaggtcc tggagcaggg cggcgtcagc agcctgttcc agaacctggg cgtcagcgtc       180 accccccatcc agagaatcgt ccttagcggc gagaacggcc tgaagatcga catccacgtc     240
atcatcccct acgagggcct gagcggcgac cagatgggcc agatcgagaa gatcttcaag       300
gtcgtctacc ccgtcgacga ccaccacttc aaggtcatcc tgcactacgg cacccctggtc      360 atcgacggcg tcacccccaa catgatcgac tacttcggta gacccatacga gggcatcgcc      420 gtcttcgacg gcaagaagat caccgtcacc ggcaccctgt ggaacggcaa caagatcatc       480
gacgagagac tgatcaaccc cgacggcagc ctgctgttca gagtcaccat caacggcgtc       540
accggctgga gactgtgcga gagaatcctg gcctaa                                 576

<210> SEQ ID NO 15
<211> LENGTH: 191
<212> TYPE: PRT
<213> ORGANISM: Artificial sequence
<220> FEATURE:
<223> OTHER INFORMATION: Synthetic Construct

<400> SEQUENCE: 15

Met Gly Val Lys Val Leu Phe Ala Leu Ile Cys Ile Ala Val Ala Glu
 1               5                  10                  15

Ala Lys Pro Thr Glu Phe Phe Thr Leu Glu Asp Phe Val Gly Asp Trp
             20                  25                  30

Arg Gln Thr Ala Gly Tyr Asn Leu Asp Gln Val Leu Glu Gln Gly Gly
         35                  40                  45

Val Ser Ser Leu Phe Gln Asn Leu Gly Val Ser Val Thr Pro Ile Gln
     50                  55                  60

Arg Ile Val Leu Ser Gly Glu Asn Gly Leu Lys Ile Asp Ile His Val
 65                  70                  75                  80

Ile Ile Pro Tyr Glu Gly Leu Ser Gly Asp Gln Met Gly Gln Ile Glu
                 85                  90                  95
```

Lys Ile Phe Lys Val Val Tyr Pro Val Asp His His Phe Lys Val
            100                 105                 110

Ile Leu His Tyr Gly Thr Leu Val Ile Asp Gly Val Thr Pro Asn Met
        115                 120                 125

Ile Asp Tyr Phe Gly Arg Pro Tyr Glu Gly Ile Ala Val Phe Asp Gly
    130                 135                 140

Lys Lys Ile Thr Val Thr Gly Thr Leu Trp Asn Gly Asn Lys Ile Ile
145                 150                 155                 160

Asp Glu Arg Leu Ile Asn Pro Asp Gly Ser Leu Leu Phe Arg Val Thr
                165                 170                 175

Ile Asn Gly Val Thr Gly Trp Arg Leu Cys Glu Arg Ile Leu Ala
            180                 185                 190

<210> SEQ ID NO 16
<211> LENGTH: 174
<212> TYPE: PRT
<213> ORGANISM: Artificial sequence
<220> FEATURE:
<223> OTHER INFORMATION: Synthetic Construct

<400> SEQUENCE: 16

Lys Pro Thr Glu Phe Phe Thr Leu Glu Asp Phe Val Gly Asp Trp Arg
1               5                   10                  15

Gln Thr Ala Gly Tyr Asn Leu Asp Gln Val Leu Glu Gln Gly Gly Val
            20                  25                  30

Ser Ser Leu Phe Gln Asn Leu Gly Val Ser Val Thr Pro Ile Gln Arg
        35                  40                  45

Ile Val Leu Ser Gly Glu Asn Gly Leu Lys Ile Asp Ile His Val Ile
    50                  55                  60

Ile Pro Tyr Glu Gly Leu Ser Gly Asp Gln Met Gly Gln Ile Glu Lys
65                  70                  75                  80

Ile Phe Lys Val Val Tyr Pro Val Asp His His Phe Lys Val Ile
                85                  90                  95

Leu His Tyr Gly Thr Leu Val Ile Asp Gly Val Thr Pro Asn Met Ile
            100                 105                 110

Asp Tyr Phe Gly Arg Pro Tyr Glu Gly Ile Ala Val Phe Asp Gly Lys
        115                 120                 125

Lys Ile Thr Val Thr Gly Thr Leu Trp Asn Gly Asn Lys Ile Ile Asp
    130                 135                 140

Glu Arg Leu Ile Asn Pro Asp Gly Ser Leu Leu Phe Arg Val Thr Ile
145                 150                 155                 160

Asn Gly Val Thr Gly Trp Arg Leu Cys Glu Arg Ile Leu Ala
                165                 170

<210> SEQ ID NO 17
<211> LENGTH: 33
<212> TYPE: DNA
<213> ORGANISM: Artificial sequence
<220> FEATURE:
<223> OTHER INFORMATION: synthetic DNA

<400> SEQUENCE: 17
gcggaattct tcacactcga agatttcgtt ggg                                    33

<210> SEQ ID NO 18
<211> LENGTH: 36
<212> TYPE: DNA
<213> ORGANISM: Artificial sequence
<220> FEATURE:

<223> OTHER INFORMATION: synthetic DNA

<400> SEQUENCE: 18
gcctctagat tacgccagaa tgcgttcgca cagccg 36

<210> SEQ ID NO 19
<211> LENGTH: 576
<212> TYPE: DNA
<213> ORGANISM: Artificial sequence
<220> FEATURE:
<223> OTHER INFORMATION: synthetic DNA

<400> SEQUENCE: 19

```
atgggagtca aagttctgtt tgccctgatc tgcatcgctg tggccgaggc caagcccacc    60
gaattcttca cactcgaaga tttcgttggg gactggcgac agacagccgg ctacaacctg   120
gaccaagtcc ttgaacaggg aggtgtgtcc agtttgtttc agaatctcgg ggtgtccgta   180
actccgatcc aaaggattgt cctgagcggt gaaaatgggc tgaagatcga catccatgtc   240
atcatcccgt atgaaggtct gagcggcgac caaatgggcc agatcgaaaa aattttttaag   300
gtggtgtacc ctgtggatga tcatcacttt aaggtgatcc tgcactatgg cacactggta   360
atcgacgggg ttacgccgaa catgatcgac tatttcggac ggccgtatga aggcatcgcc   420
gtgttcgacg gcaaaaagat cactgtaaca gggaccctgt ggaacggcaa caaaattatc   480
gacgagcgcc tgatcaaccc cgacggctcc ctgctgttcc gagtaaccat caacggagtg   540
accggctggc ggctgtgcga acgcattctg gcgtaa                              576
```

<210> SEQ ID NO 20
<211> LENGTH: 36
<212> TYPE: DNA
<213> ORGANISM: Artificial sequence
<220> FEATURE:
<223> OTHER INFORMATION: synthetic DNA

<400> SEQUENCE: 20
gcgggtacca ccatggtctt cacactcgaa gatttc 36

<210> SEQ ID NO 21
<211> LENGTH: 516
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(516)

<400> SEQUENCE: 21

```
atg gtc ttc aca ctc gaa gat ttc gtt ggg gac tgg cga cag aca gcc    48
Met Val Phe Thr Leu Glu Asp Phe Val Gly Asp Trp Arg Gln Thr Ala
1               5                   10                  15 ggc tac aac ctg gac caa gtc ctt gaa cag gga ggt gtg tcc agt ttg    96
Gly Tyr Asn Leu Asp Gln Val Leu Glu Gln Gly Gly Val Ser Ser Leu
            20                  25                  30 ttt cag aat ctc ggg gtg tcc gta act ccg atc caa agg att gtc ctg   144
Phe Gln Asn Leu Gly Val Ser Val Thr Pro Ile Gln Arg Ile Val Leu
        35                  40                  45 agc ggt gaa aat ggg ctg aag atc gac atc cat gtc atc atc ccg tat   192
Ser Gly Glu Asn Gly Leu Lys Ile Asp Ile His Val Ile Ile Pro Tyr
    50                  55                  60 gaa ggt ctg agc ggc gac caa atg ggc cag atc gaa aaa att ttt aag   240
Glu Gly Leu Ser Gly Asp Gln Met Gly Gln Ile Glu Lys Ile Phe Lys
```

```
                65                  70                  75                  80
gtg gtg tac cct gtg gat gat cat cac ttt aag gtg atc ctg cac tat        288
Val Val Tyr Pro Val Asp Asp His His Phe Lys Val Ile Leu His Tyr
                    85                  90                  95 ggc aca ctg gta atc gac ggg gtt acg ccg aac atg atc gac tat ttc        336
Gly Thr Leu Val Ile Asp Gly Val Thr Pro Asn Met Ile Asp Tyr Phe
                   100                 105                 110 gga cgg ccg tat gaa ggc atc gcc gtg ttc gac ggc aaa aag atc act        384
Gly Arg Pro Tyr Glu Gly Ile Ala Val Phe Asp Gly Lys Lys Ile Thr
                   115                 120                 125 gta aca ggg acc ctg tgg aac ggc aac aaa att atc gac gag cgc ctg        432
Val Thr Gly Thr Leu Trp Asn Gly Asn Lys Ile Ile Asp Glu Arg Leu
               130                 135                 140 atc aac ccc gac ggc tcc ctg ctg ttc cga gta acc atc aac gga gtg        480
Ile Asn Pro Asp Gly Ser Leu Leu Phe Arg Val Thr Ile Asn Gly Val
145                 150                 155                 160 acc ggc tgg cgg ctg tgc gaa cgc att ctg gcg taa                        516
Thr Gly Trp Arg Leu Cys Glu Arg Ile Leu Ala
                165                 170
```

<210> SEQ ID NO 22
<211> LENGTH: 171
<212> TYPE: PRT
<213> ORGANISM: Artificial sequence
<220> FEATURE:
<223> OTHER INFORMATION: Synthetic Construct

<400> SEQUENCE: 22

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
               100                 105                 110

Gly Arg Pro Tyr Glu Gly Ile Ala Val Phe Asp Gly Lys Lys Ile Thr
               115                 120                 125

Val Thr Gly Thr Leu Trp Asn Gly Asn Lys Ile Ile Asp Glu Arg Leu
           130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```